United States Patent
Athanas

(10) Patent No.: US 11,495,323 B2
(45) Date of Patent: Nov. 8, 2022

(54) MICROBIAL CLASSIFICATION OF A BIOLOGICAL SAMPLE BY ANALYSIS OF A MASS SPECTRUM

(71) Applicant: Thermo Finnigan LLC, San Jose, CA (US)

(72) Inventor: Michael J. Athanas, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 961 days.

(21) Appl. No.: 16/254,849

(22) Filed: Jan. 23, 2019

(65) Prior Publication Data
US 2020/0234787 A1     Jul. 23, 2020

(51) Int. Cl.
    *G16B 5/20*         (2019.01)
    *G01N 33/50*      (2006.01)
    *G01N 33/68*      (2006.01)

(52) U.S. Cl.
CPC ............ *G16B 5/20* (2019.02); *G01N 33/50* (2013.01); *G01N 33/5091* (2013.01); *G01N 33/6848* (2013.01)

(58) Field of Classification Search
CPC .......... G16B 5/20; G16B 20/00; G16B 40/20; G16B 40/10; G01N 33/5091; G01N 33/6848; G01N 33/50
USPC ......................................................... 702/27
See application file for complete search history.

(56) References Cited

U.S. PATENT DOCUMENTS

| | | | |
|---|---|---|---|
| 8,241,861 B1 * | 8/2012 | Heinecke | G01N 33/92 435/7.1 |
| 2005/0061967 A1 | 3/2005 | Shvartsburg et al. | |
| 2008/0185513 A1 * | 8/2008 | Belov | H01J 49/0031 250/288 |
| 2015/0051840 A1 | 2/2015 | Vervier et al. | |

OTHER PUBLICATIONS

Strohalm, "mMass—Open Source MS Tool", Data Processing Tools, (2010), URL: https://web.archive.org/web/20181203012131/http://www.mmass.org/features/processing.php.

AlMasoud et al., "Optimization of matrix assisted desorption/ionization time of flight mass spectrometry (MALDI-TOF-MS) for the characterization of *Bacillus* and *Brevibacillus* species", Analytica Chimica Acta 840 (2014), pp. 49-57.

Bruyne et al., "Bacterial species identification from MALDI-TOF mass spectra through data analysis and machine learning", Systemic and Applied Microbiology 34 (2011), pp. 20-29.

(Continued)

*Primary Examiner* — Kiet T Nguyen
(74) *Attorney, Agent, or Firm* — Invoke IP; Charles B. Katz

(57) ABSTRACT

Techniques for determining a microbial classification based on a mass spectrum are disclosed. A mass spectrometer generates a mass spectrum for a biological sample. A binning function is applied to the mass spectrum to generate a binned mass spectrum. As an example, a binned mass spectrum is associated with a set of bins having mass errors of the same value. A classification algorithm is applied to the binned mass spectrum to determine a microbial classification.

22 Claims, 12 Drawing Sheets

(56) References Cited

OTHER PUBLICATIONS

Ellis et al., "Rapid and quantitative detection of the microbial spoilage of meat by fourier transform infrared spectroscopy and machine learning", Applied and Environmental Microbiology, 2002, pp. 2822-2828.
Gromski et al., "Rapid and quantitative detection of the microbial spoilage of meat by fourier transform infrared spectroscopy and machine learning", Analytica Chimica Acta 829 (2014), pp. 1-8.
Swan et al., "Application of Machine Learning to Proteomics Data: Classification and Biomarker Identification in Postgenomics Biology", 2013, 17 (12) pp. 595-610.
Vervier et al., "Benchmark of structured machine learning methods for microbial identification from mass-spectrometry data", Cornell University Library, e-Print archive, https://arxiv.org/abs/1506.07251, 2015, pp. 1-12.

\* cited by examiner

Probability Vector 408

| Probability | Classification |
|---|---|
| 6.27E-04 | Haemophilus haemolyticus |
| 9.24E-04 | Staphylococcus capitis |
| 5.03E-04 | Aeromonas simiae |
| 1.05E-03 | Aeromonas media |
| 1.07E-03 | Corynebacterium argentoratens |
| 6.94E-04 | Acinetobacter junii |
| 4.52E-04 | Pseudomonas hibiscicola |
| 1.15E-03 | Enterococcus gallinarum |
| 5.91E-04 | Burkholderia thailandensis |
| 9.67E-05 | Haemophilus paragallinarum |
| 1.23E-03 | Hafnia alvei |
| 9.74E-01 | Streptococcus oralis |
| 8.11E-04 | Actinomyces israelii |
| 8.21E-04 | Acinetobacter junii |
| 1.80E-05 | Corynebacterium matruchotii |
| 3.97E-04 | Pseudomonas aeruginosa |
| 1.13E-03 | Aeromonas tecta |
| 9.89E-04 | Bacillus subtilis |
| 2.59E-04 | Staphylococcus arlettae |
| 5.06E-04 | Clostridium sordellii |
| 5.79E-04 | Aggregatibacter segnis |
| 1.31E-04 | Pseudoflavonifractor capillos |
| 4.91E-04 | Streptococcus sp (group k) |
| 2.11E-04 | Corynebacterium macginleyi |
| 7.01E-04 | Eggerthella lenta |
| 1.99E-04 | Psychrobacter immobilis |
| 1.07E-03 | Plesiomonas shigelloides |
| 8.91E-04 | Aeromonas enteropelogenes |
| 1.33E-04 | Cronobacter turicensis |
| 5.17E-04 | Enterococcus cecorum |
| 6.28E-04 | Aeromonas schubertii |
| 1.34E-04 | Providencia rettgeri |
| 7.96E-04 | Erysipelothrix rhusiopathiae |
| 1.06E-03 | Proteus hauseri |
| 5.42E-04 | Enterobacter sakazakii |
| 2.34E-04 | Acinetobacter lwoffii |
| 1.02E-03 | Citrobacter freundii |
| 9.61E-04 | Actinomyces oris |
| 1.11E-03 | Streptococcus orisratti |
| 9.93E-04 | Bacteroides vulgatus |

Fig. 4H

MICROBIAL CLASSIFICATION OF A BIOLOGICAL SAMPLE BY ANALYSIS OF A MASS SPECTRUM

TECHNICAL FIELD

The present disclosure relates to mass spectrometry. In particular, the present disclosure relates to microbial classification based on a binned mass spectrum.

BACKGROUND

Mass spectrometry is a widely used technique for analysis of a variety of samples, including samples of biological origin. Generally described, a mass spectrometer has three primary components: an ionization source that generates ions from molecules or atoms present in the sample, a set of ion optics that focuses and guides the ions through a series of vacuum chambers, and a mass analyzer that receives the ions from the ion optics, separates the ions according to their mass-to-charge ratios (m/z's), and detects the abundances of ions over a range of m/z's. Types of mass analyzers that may be employed for this purpose include (without limitation) quadrupole mass filters, time-of-flight (TOF) mass analyzers, quadrupole ion traps, and orbital electrostatic trap mass analyzers (such as the Orbitrap mass analyzer, manufactured and sold by Thermo Fisher Scientific).

For certain applications, it is useful to employ one or more stages of isolation and fragmentation, whereby ions having a specified m/z are isolated and fragmented under controlled conditions to produce product (also known as fragment) ions. This technique is variously referred to as MS/MS, tandem, or MS$^n$ mass spectrometry, and may utilize (for example) a collision cell or ion trap to fragment ions by colliding them at high energies with atoms or molecules of a neutral collision gas such as nitrogen or argon.

Mass spectrometers produce data points having three dimensions: a sequentially assigned scan number, an m/z value, and an intensity value (representative of the abundance of ions detected by the mass analyzer). For applications in which a gas or liquid chromatography system is coupled to the mass spectrometer (a GC-MS or LC-MS system) in order to provide separation of sample components prior to mass spectrometric analysis, the scan number may be mapped to chromatographic elution time. The data points may be collected into a mass spectrum, which depicts the variation of ion intensity with m/z for a specified scan number (i.e., for a particular timepoint). Additionally, the data points may be collected into ion chromatograms, showing the variation of intensity with chromatographic time for ions of a specific m/z. In mass spectra, the detected ion species appear as peaks of varying intensities.

Recently, mass spectrometry has been used as a tool for classification of microbes (e.g., bacteria, viruses and fungi) present in a sample. This technique may be employed in a clinical setting to identify the pathogen responsible for an infection and to select appropriate treatment (e.g., administration of an antibiotic or anti-viral drug effective against the pathogen). Typically, this technique involves extensive processing of mass spectra (e.g., using a combination of operations such as peak picking, deisotoping, charge state deconvolution, smoothing and cropping) to identify "fingerprints" in the mass spectra, which represent one or more ionic species that are uniquely characteristic of a particular microbe.

Peak picking is the process of identifying the important peaks in a mass spectrum, based on parameters such as signal-to-noise ratio, and intensity thresholds.

Deisotoping is the process of removing unwanted isotopes from a peak list. Since a raw mass spectrum shows abundance levels of ions of slightly different masses, the raw mass spectrum includes a peak in abundance level for different isotopes of a given element. As an example, a bromine molecule may be composed of two $^{79}$Br atoms, two $^{81}$Br atoms, or a combination of $^{79}$Br-$^{81}$Br atoms. A mass spectrum of bromine (prior to deisotoping) has an isotopic cluster with two peaks, at 79 and 81 respectively. Deisotoping the mass spectrum removes one of the two peaks and/or generates another peak that represents the two peaks.

Deconvolution is the process of extracting and/or identifying desired signals from a mass spectrum that has been complicated by interferences, noise, instrumental bias, and/or other factors. As an example, deconvolution groups together multiply-charged species (a same species in the form of different charge states). Multiply-charged species are recalculated into a singly-charged form and grouped according to mass-to-charge ratio and peak width.

Smoothing is the process of applying smoothing filters to remove signal distortion caused by chemical or electronical noise.

Cropping is the process of removing unnecessary data from a mass spectrum.

Various algorithms exist for performing the above-described processing of a mass spectrum.

While approaches involving such extensive processing of mass spectra have been partially successful, the requirement of extensive processing of the mass spectra introduces considerable complexity that may in some cases reduce the reliability of microbe classification. Furthermore, these approaches have generally not been successful for classification of microbes to the strain level, which may be necessary to determine whether an infectious agent may be resistance to a particular drug therapy. Thus, there remains a need in the art for methods by which mass spectrometry may be employed for microbe identification.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

BRIEF DESCRIPTION OF THE DRAWINGS

The embodiments are illustrated by way of example and not by way of limitation in the figures of the accompanying drawings. It should be noted that references to "an" or "one" embodiment in this disclosure are not necessarily to the same embodiment, and they mean at least one. In the drawings:

FIG. 4H illustrates an example probability vector generated by an ANN for determining a microbial classification based on a binned mass spectrum, in accordance with one or more embodiments.

DETAILED DESCRIPTION

Figure 1:
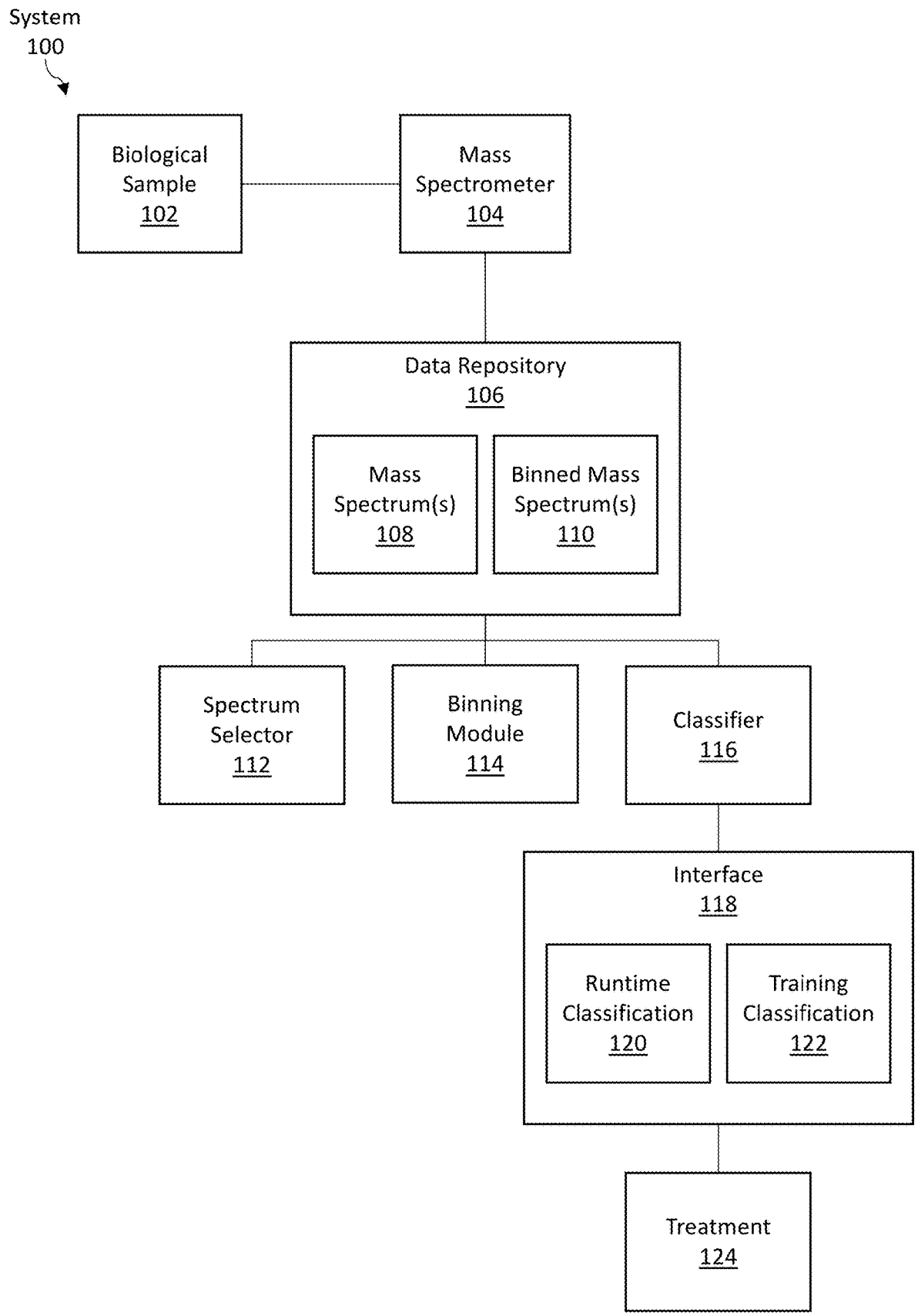
FIG. 1 illustrates a microbial classification system, in accordance with one or more embodiments.

In the following description, for the purposes of explanation, numerous specific details are set forth in order to provide a thorough understanding. One or more embodiments may be practiced without these specific details. Features described in one embodiment may be combined with features described in a different embodiment. In some examples, well-known structures and devices are described with reference to a block diagram form in order to avoid unnecessarily obscuring the present invention.

1. GENERAL OVERVIEW
2. MICROBIAL CLASSIFICATION SYSTEM ARCHITECTURE
3. DETERMINING A MICROBIAL CLASSIFICATION BASED ON A BINNED MASS SPECTRUM
4. GENERATING A CLASSIFICATION ALGORITHM USING A TRAINING SET OF BINNED MASS SPECTRA
5. EXAMPLE EMBODIMENT
6. HARDWARE OVERVIEW
7. MISCELLANEOUS; EXTENSIONS

1. General Overview

One or more embodiments include determining a microbial classification based on a binned mass spectrum. A mass spectrum associated with a biological sample is generated by a mass spectrometer. The mass spectrum indicates a respective abundance level of ions detected by the mass spectrometer for each mass-to-charge ratio. A binning function is applied to the mass spectrum to generate a binned mass spectrum. The binning function partitions the mass-to-charge ratios into a set of bins. The binned mass spectrum indicates a respective computed abundance level for each of the set of bins. A computed abundance level for a particular bin may be a sum, average, or other computational result associated with all abundance levels, indicated by the mass spectrum, that are categorized into the particular bin. A classification algorithm is applied to the binned mass spectrum to determine a microbial classification for the biological sample. The classification algorithm may include an artificial neural network (ANN). One or more actions, such as a medical treatment, may be determined based on the microbial classification. Determining a microbial classification by applying a classification algorithm to a binned mass spectrum results in a higher accuracy rate than by obtaining a "fingerprint" of a mass spectrum through extensive processing (such as, deisotoping) of the mass spectrum.

Various binning functions may be used. In an embodiment, each bin is associated with a "mass error" of the same value. A mass error of a particular bin is determined based on a lower bound and an upper bound of the particular bin. As an example, a mass error may be determined based on dividing (a) a difference between a lower bound and an upper bound of a bin by (b) an average of the lower bound and the upper bound of the bin. Additional and/or alternative binning functions may be used.

A binning function may be irrespective of isotopes associated with the biological sample. In an embodiment, each bin may include all or only a subset of abundance levels corresponding to isotopic cluster of a same ion. As an example, two abundance levels may be detected for different isotopes of a same ion. Based on a binning function, one of the two abundance level may be partitioned into one bin, and the other abundance level may be partitioned into a different bin. In an embodiment, each bin may include abundance levels corresponding to zero, one, or more ions. As an example, a single bin may include an abundance level corresponding to one icon and another abundance level corresponding to a different ion.

A microbial classification may be determined based on a binned mass spectrum without performing extensive processing. In an embodiment, a microbial classification is determined using a mass spectrum that includes all isotopes detected by a mass spectrometer. Deisotoping is not performed on the mass spectrum generated by the mass spectrometer. A binned mass spectrum is generated based on the mass spectrum. A classification algorithm is applied to the binned mass spectrum to determine a microbial classification. Accordingly, time and resources for deisotoping a mass spectrum is avoided.

In an embodiment, a microbial classification of a biological sample is determined using a single mass spectrum of the biological sample. A single mass spectrum of a specimen is generated by a mass spectrometer. A single binned mass spectrum is generated based on the single mass spectrum. A classification algorithm is applied to the single binned mass spectrum to determine a microbial classification. Accordingly, time and resources for analyzing multiple mass spectra to determine a microbial classification is avoided.

In an embodiment, a microbial classification is determined using one or more mass spectra of unfragmented ions, without using any mass spectra of fragmented ions. A mass spectrum of unfragmented ions is generated by a mass spectrometer. A binned mass spectrum is generated based on the mass spectrum of unfragmented ions. A classification algorithm is applied to the binned mass spectrum to determine a microbial classification. Accordingly, there is no need to employ fragmentation of ions and/or tandem mass spectrometry.

In an embodiment, a microbial classification is determined using a mass spectrum associated with a maximum mass-to-charge ratio threshold. A mass spectrometer that is not configured to detect above a maximum mass-to-charge ratio threshold (for example, 1,500 Daltons) generates a mass spectrum. The mass spectrometer may miss detection of one or more ions of the specimen that are above the maximum mass-to-charge ratio threshold. The mass spectrum indicates a respective abundance level for each mass-to-charge ratio below the maximum mass-to-charge ratio threshold. The mass spectrum does not provide any abundance level information above the maximum mass-to-charge ratio threshold. A binned mass spectrum is generated based on the mass spectrum. A classification algorithm is applied to the binned mass spectrum to determine a microbial classification.

One or more embodiments include generating a classification algorithm using a training set of binned mass spectra and known classification labels. A training set of mass spectra associated with one or more biological samples is generated by one or more mass spectrometers. A training set of binned mass spectra are generated based on the training set of mass spectra. Each of the binned mass spectra is associated with a classification label indicating a microbial classification of the biological sample associated with the binned mass spectrum. A machine learning algorithm is applied to the training set of binned mass spectra and the associated labels to generate a classification algorithm. As an example, a machine learning algorithm may generate an ANN. The machine learning algorithm may, for example, determine attributes of the binned mass spectra to be used as input to the ANN, adjusts weights used in the ANN, determine a number of layers used in the ANN, and/or determine connections between neurons of the ANN. The classification algorithm may be used to determine a microbial classification of a biological sample based on a binned mass spectrum associated with the biological sample.

In an embodiment, the training set of mass spectra includes mass spectra of unfragmented ions, without including mass spectra of fragmented ions. In an embodiment, the training set of mass spectra does not include any mass spectra that provide abundance information above a maximum mass-to-charge ratio threshold. In an embodiment, the training set of mass spectra are not subjected to any deisotoping process. The classification algorithm is generated without performing any deisotoping process.

One or more embodiments described in this Specification and/or recited in the claims may not be included in this General Overview section.

2. Microbial Classification System Architecture

FIG. 1 illustrates a microbial classification system, in accordance with one or more embodiments. As illustrated in FIG. 1, a system 100 includes a biological sample 102, a mass spectrometer 104, a data repository 106, a spectrum selector 112, a binning module 114, a classifier 116, an interface 118, and a treatment 124. In one or more embodiments, the system 100 may include more or fewer components than the components illustrated in FIG. 1. The components illustrated in FIG. 1 may be local to or remote from each other. The components illustrated in FIG. 1 may be implemented in software and/or hardware. Each component may be distributed over multiple applications and/or machines. Multiple components may be combined into one application and/or machine. Operations described with respect to one component may instead be performed by another component.

In one or more embodiments, a biological sample 102 may include one or more microbes, such as bacteria, viruses, or fungi. The sample 102 may be a biofluid, such as blood plasma, urine, saliva, sweat, breast milk, or cerebrospinal fluid, or may be a tissue extract. The sample 102 may be subjected to one or more sample preparation steps prior to analysis by mass spectrometer 104 intended to improve detection of particular analytes. These preparation steps may include cell lysis, reduction, alkylation, and proteolytic digestion, as well as enrichment, separation and purification.

As known in the art and discussed in the introduction, a mass spectrometer 104 includes an ion source for generating ions from molecules (including biological molecules such as peptides and proteins), ion optics for focusing and guiding the ions, and a mass analyzer for separating the ions according to their mass-to-charge ratios (m/z's) and detecting the separated ions. The mass spectrometer may also include a fragmentation device, such as a collision cell, for fragmenting ions in a controlled manner to produce product (fragment) ions for analysis. The mass analyzer outputs a signal representative of the variation of ion abundance with m/z (note that the term "mass" is commonly used in the industry, and sometimes herein, as shorthand for mass-to-charge ratio, and the interchangeability of the two terms should be recognized).

In one or more embodiments, a data repository 106 is any type of storage unit and/or device (e.g., a file system, database, collection of tables, or any other storage mechanism) for storing data. Further, a data repository 106 may include multiple different storage units and/or devices. The multiple different storage units and/or devices may or may not be of the same type or located at the same physical site. Further, a data repository 106 may be implemented or executed on the same computing system as a spectrum selector 112, binning module 114, and/or classifier 116. Alternatively, or additionally, a data repository 106 may be implemented or executed on a computing system separate from a spectrum selector 112, binning module 114, and/or classifier 116. The data repository 104 may be communicatively coupled to the spectrum selector 112, binning module 114, and/or classifier 116 via a direct connection or via a network.

Information describing one or more mass spectra 108 and one or more binned mass spectra 110 may be implemented across any of components within the system 100. However, this information is illustrated within the data repository 104 for purposes of clarity and explanation.

In one or more embodiments, a mass spectrum 108 is a plot of abundance level of ions, per mass-to-charge ratio (m/z), detected during a scan. A mass spectrum 108 may be presented as a vertical bar graph. Each bar corresponds to a specific mass-to-charge ratio. A length of a bar indicates the relative abundance of ions of the corresponding mass-to-charge ratio.

In one or more embodiments, a binned mass spectrum 110 is a plot of computed abundance level of ions, per bin, detected during a scan. A binned mass spectrum 110 may be presented as a vertical bar graph. Each bar corresponds to a specific bin. A length of a bar indicates the relative computed abundance of ions associated with the corresponding bin. A computed abundance level for a particular bin may be a sum, average, and/or other computational result associated with all abundance levels, indicated by the mass spectrum 108, that are categorized into the particular bin.

In an embodiment, each bin is associated with a mass error of the same value. The value of the mass error may be specified by a person and/or an application. A mass error of a particular bin is determined based on applying a mass error formula to a lower bound and an upper bound of the particular bin. The value of the lower bound and/or upper bound are set such that the mass error equals the value specified by the person and/or the application.

As an example, a mass error of a particular bin may be determined based on dividing (a) a difference between a lower bound $m_l$ and an upper bound $m_u$ of the particular bin by (b) an average of the lower bound $m_l$ and the upper bound $m_u$ of the particular bin. The mass error (ME) may be a parts per million (ppm) representation of the above quotient, as follows:

$$ME = \frac{m_u - m_l}{(m_u + m_l)/2} \times 10^6.$$

In an embodiment, a difference between a lower bound and an upper bound of a bin may be referred to as a "width" of the bin. Each bin may be associated with a different width.

As an example, for a mass error of 100 ppm, the following bins may be identified:

| Bin | Lower Bound (m/z) | Upper Bound (m/z) | Width |
|---|---|---|---|
| Bin 0 | 500.0000 | 500.0010 | 0.0010 |
| Bin 1 | 500.0010 | 500.0030 | 0.0020 |
| Bin 2 | 500.0030 | 500.0060 | 0.0030 |
| Bin 3 | 500.0060 | 500.0100 | 0.0040 |
| Bin 4 | 500.0100 | 500.0150 | 0.0050 |

In the above example, each bin is associated with a same mass error of 100 ppm. However, each bin is associated with a different width.

In other embodiments, a set of bins may be defined differently. As an example, each bin may have the same width. A width may be specified by a person and/or an application. As another example, each bin may be associated with the same mass error value, however the mass error formula may be different than the formula presented above (examples are detailed below).

In one or more embodiments, a spectrum selector 112 refers to hardware and/or software configured to perform operations described herein for selecting a mass spectrum 108 to be used for determining a microbial classification 120. Examples of operations for selecting a mass spectrum 108 are described below with reference to FIG. 2.

In one or more embodiments, a binning module 114 refers to hardware and/or software configured to perform operations described herein for generating a binned mass spectrum 110, based on a mass spectrum 108, for determining a microbial classification 120. Examples of operations for generating a binned mass spectrum 110 based on a mass spectrum 108 are described below with reference to FIG. 2.

In one or more embodiments, a classifier 116 refers to hardware and/or software configured to perform operations described herein for determining a microbial classification 120 based on a binned mass spectrum 110. Examples of operations for determining a microbial classification 120 based on a binned mass spectrum 110 are described below with reference to FIG. 2.

In one or more embodiments, a classifier 116 uses a classification algorithm that is determined by a machine learning algorithm. The machine learning algorithm is applied to a training set of binned mass spectra 110 to determine the classification algorithm. Examples of classification algorithm may include an artificial neural network (ANN), a regression model, a clustering analysis, a support vector machine, and/or a Bayseian network. Examples of operations for generating a classification algorithm, for determining a microbial classification 120, using on a training set of binned mass spectra 110 are described below with reference to FIG. 3.

In an embodiment, a classifier 116 uses an ANN, which includes a collection of connected units or nodes, which are called artificial neurons. Each connection transmits a signal from one artificial neuron to another. An artificial neuron that processes a received signal to transmit another signal to another artificial neuron. Artificial neurons may be aggregated into layers. Different layers may perform different kinds of transformations on their inputs.

One type of ANN is a convolutional neural network. Convolutional neural networks may be used to process data that come in the form of multiple arrays, such as a color image composed of three two-dimensional arrays containing pixel intensities in three color channels. An example architecture of a conventional neural network is structured as a series of stages. The first few stages are composed of two types of layers: convolutional layers and pooling layers. A convolutional layer divides a two-dimensional array into windows of a specific dimension of local pixels. The convolution layer applies a convolution operation to each window to reduce the information to a smaller number of values. The convolution layer passes the result to the next layer in the ANN. The convolution emulates the response of an individual neuron to visual stimuli. A pooling layer combines the outputs of neuron clusters at one layer into a single neuron in the next layer. For example, max pooling uses the maximum value from each of a cluster of neurons at the prior layer. An example of a conventional neural network is the u-net. The u-net is described in Ronneberger et al., *U-Net: Convolutional Networks for Biomedical Image Segmentation*, MEDICAL IMAGE COMPUTING AND COMPUTER-ASSISTED INTERVENTION—MICCAI 2015, at 234-241 (2015), which is hereby incorporated by reference. Each neuron in the ANN is associated with a numerical weight and/or bias, which is adjusted in the course of neural network training. Additional and/or alternative layers include, for example, a dropout layer, a dense layer, and/or an activation layer.

A convolutional neural network may be customized to process a one-dimensional input, such as a binned mass spectrum 110. A convolutional layer divides the one-dimensional array into windows of a specific length. The convolution layer applies a convolution operation to each window to reduce the information to a smaller number of values. The convolution layer passes the result to the next layer in the ANN. Layers such as a pooling layer, a dropout layer, a dense layer, and/or an activation layer may also be used.

An ANN is configured to determine a probability vector for a binned mass spectrum. The probability vector indicates a respective probability for each candidate microbial classification for the biological sample 102. A candidate microbial classification associated with the highest probability is determined as a runtime classification 120 for the biological sample 102. Additional information may be calculated and reported such as a statistic representing the confidence of the reported probability.

In an embodiment, a classifier 116 is associated with one or more parameters. The parameters describe a training set of binned mass spectra 110 used to train the classification algorithm. Additionally or alternatively, the parameters describe a machine learning algorithm used to train the classification algorithm. A parameter may be configured by a person and/or an application. Examples of parameters are described below. Additional or alternative parameters may be used.

As an example, a parameter of a classifier may be a mass error value associated with a training set of binned mass spectra. Bins of the training set of binned mass spectra are associated with mass errors of the same mass error value. The mass error value may be configured by a person and/or an application. The mass error value may be, for example, determined based on abundance levels indicated by the mass spectra that form the basis of the training set of binned mass spectra.

As an example, a parameter of a classifier may be a lower bound of a first bin (the bin associated with the lowest mass-to-charge ratio, as compared with other bins) associated with a training set of binned mass spectra. The lower bound of the first bin may be configured by a person and/or an application. The lower bound of the first bin may be, for example, determined based on abundance levels indicated by the mass spectra that form the basis of the training set of binned mass spectra. The lower bound of the remaining bins may be determined based on the lower bound of the first bin and the mass error value set for the training set of binned mass spectra.

As an example, a parameter of a classifier may be a mass range associated with a training set of binned mass spectra. The training set of binned mass spectra do not include any abundance information for bins associated with a mass-to-charge ratio below a threshold value. The training set of binned mass spectra do not include any abundance information for bins associated with a mass-to-charge ratio above another threshold value. The two threshold values constitute the mass range associated with the training set of binned mass spectra. The mass range may be configured by a person and/or an application. The mass range may be determined, for example, based on the functionality of a mass spectrometer used to generate the mass spectra that form the basis of the training set of binned mass spectra. The mass spectrometer might not have the functionality to detect ions above a certain mass-to-charge ratio.

As an example, a parameter of a classifier may be a convolution window size. The convolution window size determines how convolution is performed by an ANN. The convolution window size may be configured by a person and/or an application.

In an embodiment, a spectrum selector 112, binning module 114, and/or classifier 116 is implemented on one or more digital devices. The term "digital device" generally refers to any hardware device that includes a processor. A digital device may refer to a physical device executing an application or a virtual machine. Examples of digital devices include a computer, a tablet, a laptop, a desktop, a netbook, a server, a web server, a network policy server, a proxy server, a generic machine, a function-specific hardware device, a mainframe, a television, a content receiver, a set-top box, a printer, a mobile handset, a smartphone, and/or a personal digital assistant (PDA).

In one or more embodiments, an interface 118 refers to hardware and/or software configured to facilitate communications with a classifier 116. In an embodiment, an interface 118 is a user interface that presents user interface elements to provide information. Additionally or alternatively, the user interface presents user interface elements to receive information as user input. Examples of user interfaces include a graphical user interface (GUI), a command line interface (CLI), a haptic interface, and a voice command interface. Examples of user interface elements include checkboxes, radio buttons, dropdown lists, list boxes, buttons, toggles, text fields, date and time selectors, command lines, sliders, pages, and forms. In an embodiment, an interface 118 is an application programming interface (API) that provides information to and/or receives information from another application.

In one or more embodiments, an interface 118 provides and/or receives a runtime classification 120 and a training classification 122. A runtime classification 120 and/or a training classification 122 identifies a genus and/or species of a microbe included in a biological sample 102.

A runtime classification 120 is a microbial classification that is determined by a classifier 116. The classifier 116 determines the runtime classification 120 by applying a classification algorithm to a binned mass spectrum 110. A runtime classification 120 may be accurate or inaccurate. The classifier 116 may also report a statistic describing the level of confidence associated with a runtime classification 120, such as a 95% confidence interval.

A training classification 122 is a microbial classification that is determined by a person who helps generate and/or train a classifier 116. Additionally or alternatively, a training classification 122 is a microbial classification that is determined by an application with external knowledge about a biological sample 102.

A training classification 122 is used to train a classifier 116 through machine learning. A training classification 122 of a biological sample 102 may or may not match a runtime classification 120, previously determined by a classifier 116, for the same biological sample 102. In a training set of mass spectra 108, each mass spectrum 108 is associated with a label and/or other information indicating a training classification 122 of the corresponding biological sample 102. In a training set of binned mass spectra 110, each binned mass spectrum 110 is associated with a label and/or other information indicating a training classification 122 of the corresponding biological sample 102. In an embodiment, a machine learning process attempts to generate a classifier 116 that produces a runtime classification 120 that best matches the training classification 122 for each binned mass spectrum.

3. Determining a Microbial Classification Based on a Binned Mass Spectrum

Figure 2:
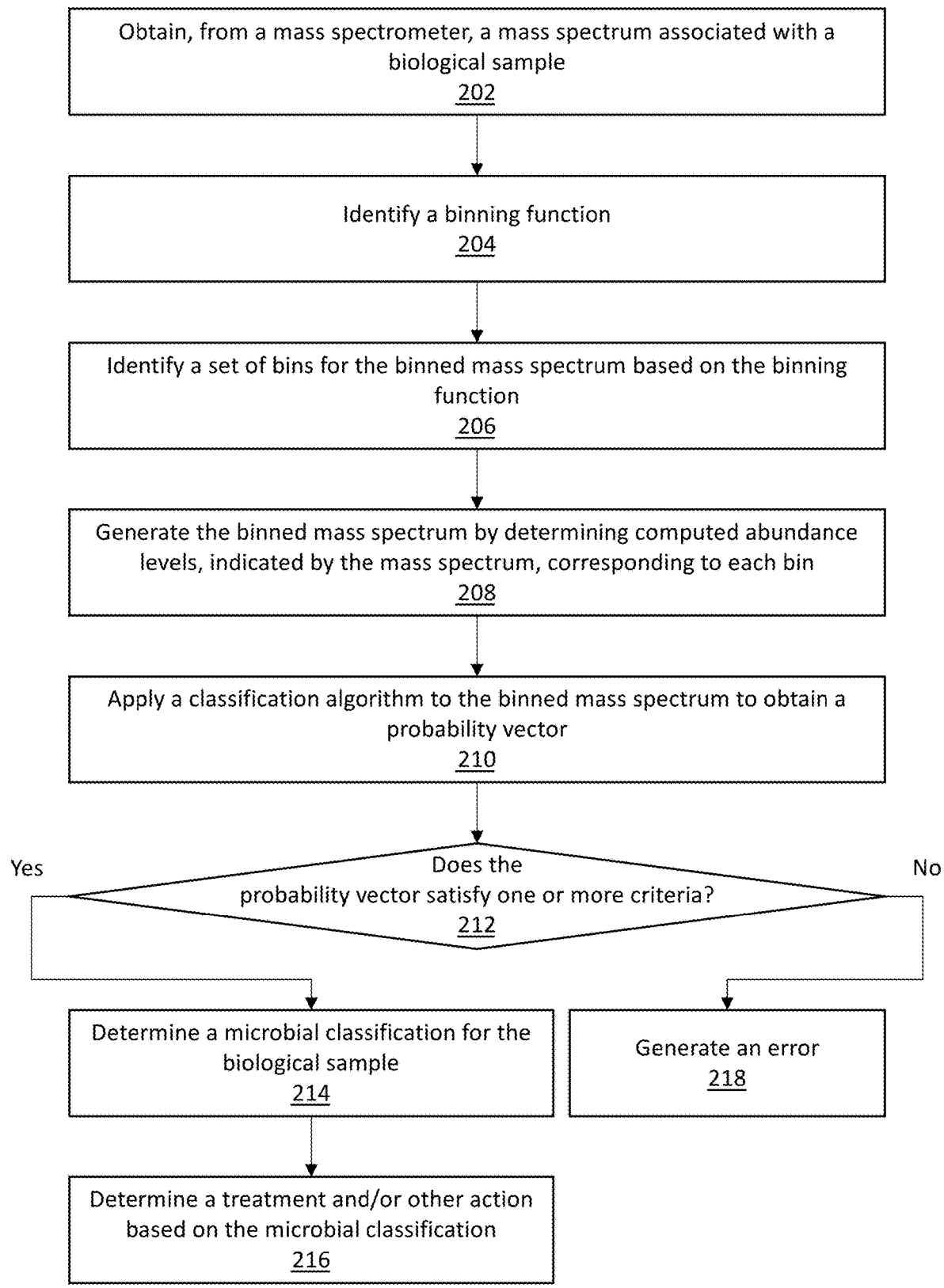
FIG. 2 illustrates an example set of operations for determining a microbial classification based on a binned mass spectrum, in accordance with one or more embodiments.

FIG. 2 illustrates an example set of operations for determining a microbial classification based on a binned mass spectrum, in accordance with one or more embodiments. One or more operations illustrated in FIG. 2 may be modified, rearranged, or omitted all together. Accordingly, the particular sequence of operations illustrated in FIG. 2 should not be construed as limiting the scope of one or more embodiments.

One or more embodiments include obtaining, from a mass spectrometer, a mass spectrum associated with a biological sample (Operation 202). A mass spectrometer performs one or more MS scans on a biological sample. Each scan produces a mass spectrum.

A spectrum selector obtains a set of one or more mass spectra from the mass spectrometer. The spectrum selector selects a mass spectrum from the set of mass spectra based on one or more factors, as further described below.

In an embodiment, the mass spectrometer performs multiple MS scans on a specimen. The mass spectrometer generates a chromatogram indicating the abundance levels of ions detected at every time interval for the multiple MS scans. Each MS scan produces a mass spectrum. The spectrum selector obtains the chromatogram and the set of mass spectra. The spectrum selector selects a mass spectrum from the set of mass spectra based on information indicated by the chromatogram. As an example, the spectrum selector may select the mass spectrum that was captured during a time interval associated with the highest abundance levels, as indicated by the chromatogram.

In an embodiment, the mass spectrometer performs tandem mass spectrometry to produce both a mass spectrum of unfragmented ions and a mass spectrum of fragmented ions. The spectrum selector selects a mass spectrum of unfragmented ions; the spectrum selector does not select a mass spectrum of fragmented ions. In an alternative embodiment, the mass spectrometer does not generate a mass spectrum of fragmented ions. The mass spectrometer might not have the functionality to perform tandem mass spectrometry. In this scenario, the spectrum selector need not make any selection based on unfragmented ions and fragmented ions.

In an embodiment, the mass spectrometer performs a single MS scan to generate a single mass spectrum. The mass spectrometer does not perform multiple MS scans to generate multiple mass spectra. Therefore, the spectrum selector simply obtains the single mass spectrum from the mass spectrometer.

One or more embodiments include identifying a binning function (Operation 204). A data repository stores one or more binning functions. A binning function to be used may be determined by a person and/or an application.

In an embodiment, a binning module selects one of the binning functions based on a parameter associated with a classification algorithm to be applied to the binned mass spectrum. The parameter of the classification algorithm indicates the binning function applied to a training set of mass spectra to generate a training set of binned mass spectra. (As further described below with reference to FIG. 3, the classification algorithm was generated based on the training set of binned mass spectra.) The binning function associated with the training set of binned mass spectra is used as the binning function for the binned mass spectrum of the biological sample to be classified by the classification algorithm.

In another embodiment, a binning module selects one of the binning functions based on an attribute associated with the mass spectrum obtained at Operation 202. As an example, a binning function may be selected based on a type of a mass spectrometer used to generate the mass spectrum. As another example, a binning function may be selected based on a signal-to-noise ratio associated with the mass spectrum. As another example, a binning function may be selected based on a type of the biological sample associated with the mass spectrum.

Examples of binning functions are described below. Additional and/or alternative binning functions may be used.

In an embodiment, a binning function partitions mass-to-charge ratios into bins associated with mass errors of the same value. The value for the mass errors may be determined by a person and/or an application.

In an embodiment, the value for the mass errors is determined based on a parameter associated with a classification algorithm to be applied to the binned mass spectrum. The parameter of the classification algorithm indicates a mass error value associated with a training set of binned mass spectra. (As further described below with reference to FIG. 3, the classification algorithm was generated based on the training set of binned mass spectra.) The mass error value associated with the training set of binned mass spectra is used as the mass error value for the binned mass spectrum of the biological sample to be classified by the classification algorithm. In other embodiments, the value of the mass errors for the binned mass spectrum may be determined based on additional and/or alternative factors.

In an embodiment, a binning function partitions mass-to-charge ratios into bins of the same width. The width may be determined by a person and/or an application.

One or more embodiments include identifying a set of bins for the binned mass spectrum based on the binning function (Operation 206). The binning module applies the binning function to the mass spectrum.

Based on the binning function, the binning module determines a lower bound of a first bin (the bin associated with the lowest mass-to-charge ratio). Additionally or alternatively, the binning module determines an upper bound of a last bin (the bin associated with the highest mass-to-charge ratio). The "mass range" of the binned mass spectra may be used herein to refer to the range of mass-to-charge ratios between the lower bound of the first bin and the upper bound of the last bin.

The lower bound of the first bin and/or the upper bound of the last bin may be determined by a person and/or an application. In an embodiment, the lower bound of the first bin is determined based on a parameter associated with a classification algorithm to be applied to the binned mass spectrum. The parameter of the classification algorithm indicates a lower bound of a first bin associated with a training set of binned mass spectra. (As further described below with reference to FIG. 3, the classification algorithm was generated based on the training set of binned mass spectra.) The lower bound of the first bin associated with the training set of binned mass spectra is used as the lower bound of the first bin for the binned mass spectrum of the biological sample to be classified by the classification algorithm. In other embodiments, the lower bound of the first bin for the binned mass spectrum may be determined based on additional and/or alternative factors. Similarly, the upper bound of the last bin is determined based on a parameter associated with the classification algorithm to be applied to the binned mass spectrum, or determined based on additional and/or alternative factors.

Based on the binning function, the binning module determines an upper bound of the first bin. In an embodiment, the binning function generates bins associated with the same mass error value. The binning module determines the upper bound of the first bin such that the first bin is associated with the specified mass error value. In an embodiment, the binning function generates bins associated with the same width. The binning module determines the upper bound of the first bin such that the first bin is associated with the specified width.

Subsequently, the upper bound of the first bin is set as a lower bound of the second bin. The binning module then iterates the process to determine an upper bound of the second bin. Hence, the above process may be iterated such that lower bounds of each of a set of bins are iteratively determined. The above process is iterated until the upper bound of the last bin is reached.

As an example, a binning function may generate a set of bins such that a mass error of each bin is equal to a same mass error value. Based on the binning function, a binning module may set a lower bound and/or an upper bound of each bin, such that a mass error of each bin is equal to the mass error value.

In a specific example, a mass error of a particular bin may be determined based on dividing (a) a difference between a lower bound $m_l$ and an upper bound $m_u$ of the particular bin by (b) an average of the lower bound $m_l$ and the upper bound $m_u$ of the particular bin. The mass error (ME) may be a parts per million (ppm) representation of the above quotient, as follows:

$$ME = \frac{m_u - m_l}{(m_u + m_l)/2} \times 10^6.$$

Solving for the upper bound $m_u$:

$$m_u = m_l \times \frac{1+k}{1-k},$$

wherein $k = ME/2/10^6$.

Since an upper bound of a particular bin (bin i) is a lower bound of the next bin (bin i+1), the lower bound $m_{i+1}$ of the next bin may be computed based on a lower bound $m_i$ of the particular bin, as follows:

$$m_{i+1} = m_i \times \frac{1+k}{1-k}.$$

Additionally or alternatively, a lower bound $m_n$ of a particular bin ($bin_n$) is determined based on the lower bound $m_0$ of the first bin, as follows:

$$m_n = m_0 \times \left(\frac{1+k}{1-k}\right)^n.$$

Hence, lower bounds of the set of bins may be as follows:

| Bin | Lower Bound (m/z) |
| --- | --- |
| Bin 0 | $m_0$ |
| Bin 1 | $m_0 \times \left(\frac{1+k}{1-k}\right)$ |
| Bin 2 | $m_0 \times \left(\frac{1+k}{1-k}\right)^2$ |
| Bin 3 | $m_0 \times \left(\frac{1+k}{1-k}\right)^3$ |
| Bin 4 | $m_0 \times \left(\frac{1+k}{1-k}\right)^4$ |

Additional and/or alternative methods for identifying the set of bins may be used. As an example, a different mass error formula may be used for defining a mass error of a bin. Examples of different calculations of mass error include:

$$ME = \frac{m_u - m_l}{(m_u + m_l)/2} \times 10^2;$$

$$ME = \frac{m_u - m_l}{(m_u + m_l)/2};$$

$$ME = \frac{m_u - m_l}{m_u} \times 10^6;$$

$$ME = \frac{m_u - m_l}{m_l} \times 10^6.$$

One or more embodiments include generating the binned mass spectrum by determining computed abundance levels, indicated by the mass spectrum, corresponding to each bin (Operation 208). The binning module determines abundance levels corresponding to mass-to-charge ratios within each bin, as indicated by the mass spectrum. In an embodiment, a mass-to-charge ratio that is (a) equal to or greater than a lower bound of a particular bin and (b) less than an upper bound of the particular bin falls within the particular bin. In an alternative embodiment, a mass-to-charge ratio that is (a) greater than a lower bound of a particular bin and (b) equal to or less than an upper bound of the particular bin falls within the particular bin.

The binning module determines a computed abundance level for a particular bin based on abundance levels corresponding to mass-to-charge ratios within the particular bin. The computed abundance level may be an aggregation of the abundance levels corresponding to mass-to-charge ratios within the particular bin. The computed abundance level may be a sum, average, and/or other computational result associated with the abundance levels corresponding to mass-to-charge ratios within the particular bin.

As an example, a mass spectrum may indicate: (a) an abundance level of 50 at a mass-to-charge ratio of 500.03 Da; (b) an abundance level of 60 at a mass-to-charge ratio of 500.08 Da; and (c) an abundance level of 55 at a mass-to-charge ratio of 500.12 Da. A first bin may range from a mass-to-charge ratio of 500.01 Da to a mass-to-charge ratio of 500.10 Da. A second bin may range from a mass-to-charge ratio of 500.10 Da to a mass-to-charge ratio of 500.23 Da. Hence, the abundance levels of 50 and 60 at mass-to-charge ratios of 500.03 Da and 500.08 Da, respectively, may fall into the first bin. The abundance levels of 50 and 60 may be aggregated to determine that an aggregated abundance level of the first bin is 110 (50+60). The abundance level of 55 at the mass-to-charge ratio of 500.12 Da may fall into the second bin. The abundance level of 55 may be determined as an aggregated abundance level of the second bin. (This example indicates that the mass-to-charge ratio has the units of mass, specifically, Daltons. Note that mass-to-charge ratio and/or mass can be measured with metrics other than Daltons.)

One or more embodiments include applying a classification algorithm to the binned mass spectrum to obtain a probability vector (Operation 210). A classifier applies a classification algorithm to the binned mass spectrum.

In an embodiment, the classification algorithm uses an artificial neural network (ANN). The ANN receives the binned mass spectrum as an input. The ANN may apply a same convolution window size to the binned mass spectrum as the convolution window size that was applied to a training set of mass spectra during training. The ANN determines a probability that the biological sample is associated with each candidate microbial classification. The ANN outputs a probability vector indicating the probabilities for the candidate microbial classifications.

Additional and/or alternative classification algorithms may be used. As an example, a classification algorithm may generate a probability vector that indicates a probability that the biological sample is associated with a particular microbial classification, without indicating the probability that the biological sample is associated with any other microbial classification.

In an embodiment, the classification algorithm is applied to the binned mass spectrum without first performing any pre-processing (such as, deisotoping) on the mass spectrum and/or the binned mass spectrum.

In an embodiment, the classification algorithm is applied to a single mass spectrum. The classification algorithm does not take any other mass spectra as input. The classification algorithm determines a microbial classification based on the single mass spectrum.

One or more embodiments include determining whether the probability vector satisfies one or more criteria (Operation 212). The classifier evaluates the probability vector and determines whether the probability vector satisfies one or more criteria. The criteria may have been previously specified by a person and/or an application.

In an embodiment, a criteria is that the highest probability indicated by the probability vector is above a threshold value. The threshold value may be set by a person and/or an application. Additionally or alternatively, the threshold value may be determined based on one or more probabilities indicated by the probability vector. As an example, the threshold value may be a certain value above a second highest probability indicated by the probability vector. As another example, the threshold value may be a certain value above an average of the probabilities indicated by the probability vector. Additionally or alternatively, the threshold value may be determined based on historical accuracy of the classification algorithm. As an example, based on historical applications of the classification algorithm, a probability above a certain threshold value may be associated with a particular accuracy rate. The threshold value may be used as the criteria for accepting the probability vector associated with the biological sample.

In an embodiment, a criteria is that the probabilities indicated by the probability vector match a certain statistical distribution. In an embodiment, a criteria is that a certain number of probabilities indicated by the probability vector be below a threshold value. In an embodiment, a criteria is that a second highest probability indicated by the probability vector is below a threshold value. Additional and/or alternative criteria may be used.

If the probability vector satisfies the criteria, the system determines a microbial classification for the biological sample (Operation 214). The classifier determines the candidate microbial classification associated with the highest probability as the microbial classification for the biological sample. The classifier may cause the microbial classification to be presented at a user interface. Additionally and/or alternatively, the classifier may transmit the microbial classification to another application.

One or more embodiments include determining a treatment and/or other action based on the microbial classification (Operation 216). A treatment and/or action is determined based on the microbial classification. A treatment may be administered by a medical professional, a medical device, and/or any other device.

In an embodiment, mappings between microbial classifications and actions are stored in a data repository. The system executes a look-up operation on the mappings to determine an action corresponding to the microbial classification determined at Operation 214. In an embodiment, a set of rules are used for determining an action based on a microbial classification. The set of rules may accept one or more inputs in addition to the microbial classification determined at Operation 214. Additional and/or alternative methods for determining a treatment and/or action may be used.

If the probability vector does not satisfy the criteria, the system generates an error (Operation 218). The classifier generates an error indicating that the probability vector does not satisfy the criteria. The classifier may request the spectrum selector to obtain and/or select a different mass spectrum for analysis.

In an embodiment, a classifier applies a classification algorithm to a first binned mass spectrum of the biological sample to generate a first probability vector. In response to determining that the first probability vector does not satisfy a criteria, the classifier requests a second binned mass spectrum. The second binned mass spectrum and the first binned mass spectrum may be generated by applying different binning functions (such as different mass error values) to the same mass spectrum. Alternatively, the second binned mass spectrum and the first binned mass spectrum may be generated based on different mass spectra of the same biological sample. The classifier applies the classification algorithm to the second binned mass spectrum of the biological sample to generate a second probability vector. The criteria for accepting the second probability vector may be adjusted based on probabilities indicated by the first probability vector and/or the second probability vector. As an example, a criteria for accepting the second probability vector may require (a) the highest probabilities respectively indicated by the first probability vector and the second probability vector are associated with the same candidate microbial classification, or (b) the highest probability indicated by the second probability vector is above a threshold value. Then the microbial classification associated with the highest probability indicated by the second probability vector is determined as the microbial classification for the biological sample.

Figure 3:
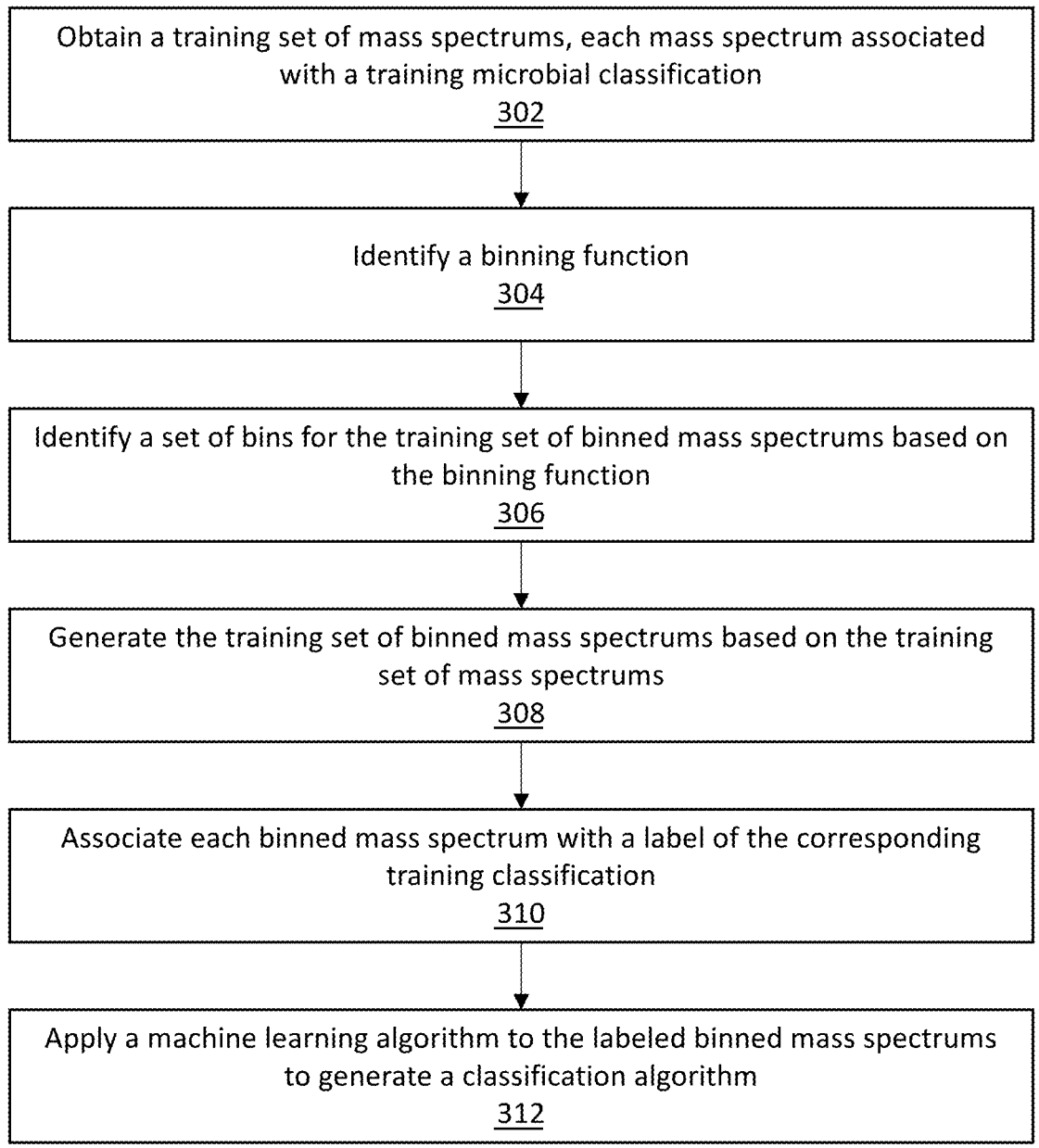
FIG. 3 illustrates an example set of operations for generating a classification algorithm using a training set of binned mass spectra, in accordance with one or more embodiments.

4. Generating a Classification Algorithm Using a Training Set of Binned Mass Spectra FIG. 3 illustrates an example set of operations for generating a classification algorithm using a training set of binned mass spectra, in accordance with one or more embodiments. One or more operations illustrated in FIG. 3 may be modified, rearranged, or omitted all together. Accordingly, the particular sequence of operations illustrated in FIG. 3 should not be construed as limiting the scope of one or more embodiments.

One or more embodiments include obtaining a training set of mass spectra, each mass spectrum associated with a training microbial classification (Operation 302). One or more mass spectrometers perform MS scans on one or more biological samples. Each scan produces a mass spectrum. The mass spectra constitute a training set of mass spectra.

In an embodiment, a person identifies a microbial classification associated with a biological sample. The person enters user input indicating a microbial classification of the biological sample. The microbial classification entered by the person is a training classification of the biological sample. The training classification is stored as a label and/or other information associated with one or more mass spectra generated based on MS scans of the biological sample.

In another embodiment, an application identifies a microbial classification associated with a biological sample based on external knowledge about the biological sample. The microbial classification determined by the application is a training classification of the biological sample. The application causes the training classification to be stored as a label and/or other information associated with one or more mass spectra generated based on MS scans of the biological sample.

One or more embodiments include identifying a binning function (Operation 304). A data repository stores one or more binning functions. A binning function to be used may be determined by a person and/or an application. In an embodiment, a binning function is selected based on an attribute associated with the training set of mass spectra. As an example, a binning function may be selected based on a type of a mass spectrometer used to generate at least one of the training set of mass spectrum. As another example, a binning function may be selected based on a signal-to-noise ratio associated with at least one of the training set of mass spectra. As another example, a binning function may be selected based on a type of the biological sample associated with at least one of the training set of mass spectra.

Various binning functions may be used, as described above. A same binning function may be applied to each of the training set of mass spectra. Additionally or alternatively, a different binning function may be applied to each of the training set of mass spectra.

In an embodiment, a binning function partitions mass-to-charge ratios into bins associated with mass errors of the same value. The value for the mass errors may be determined by a person and/or an application.

In an embodiment, a mass error value may be determined based on abundance levels indicated by the training set of mass spectra. As an example, a higher mass error value may be used if the abundance levels indicated by the training set of mass spectra are more evenly distributed across a wider range of mass-to-charge ratios.

One or more embodiments include identifying a set of bins for the training set of binned mass spectra based on the binning function (Operation 306). A binning function is applied to each of the training set of mass spectra.

Based on the binning function, a lower bound of a first bin (the bin associated with the lowest mass-to-charge ratio) is determined. Additionally or alternatively, an upper bound of a last bin (the bin associated with the highest mass-to-charge ratio) is determined.

The lower bound of the first bin and/or the upper bound of the last bin may be determined by a person and/or an application. In an embodiment, the lower bound of the first bin may be determined based on abundance levels indicated by the training set of mass spectra. As an example, the lower bound of the first bin may be determined based on the lowest mass-to-charge ratio corresponding to an abundance level above a threshold value, as indicated by the training set of mass spectra. For example, the lower bound of the first bin may be equal to the lowest mass-to-charge ratio corresponding to an abundance level above a threshold value of 50. A first mass spectrum may indicate an abundance level of 40 at a mass-to-charge ratio of 500.23 Da, and an abundance level of 60 at a mass-to-charge ratio of 500.25 Da. A second mass spectrum may indicate an abundance level of 45 at a mass-to-charge ratio of 499.88 Da. The abundance levels at the mass-to-charge ratios of 499.88 Da and 500.23 Da are 45 and 40, respectively. The abundance levels at the mass-to-charge ratios of 499.88 Da and 500.23 Da do not satisfy the threshold value of 50. The abundance level at the mass-to-charge ratio of 500.25 Da is 60. The abundance level at the mass-to-charge ratio of 500.25 Da does satisfy the threshold value of 50. Therefore, the mass-to-charge ratio of 500.25 Da may be determined as the lower bound of the first bin. Additional and/or alternative factors may be used for determining the lower bound of the first bin. Similarly, the upper bound of the last bin is determined based on abundance levels indicated by the training set of mass spectra, or determined based on additional and/or alternative factors. As an example, the lower bound of the first bin and/or the upper bound of the last bin may be determined based on a functionality of the mass spectrometer used to generate the mass spectra. The lower bound of the first bin may be determined based on a lower bound of the mass-to-charge ratio that is detectable by the mass spectrometer. The upper bound of the last bin may be determined based on an upper bound of the mass-to-charge ratio that is detectable by the mass spectrometer.

Based on the binning function, an upper bound of the first bin is determined. In an embodiment, the binning function generates bins associated with the same mass error value. The upper bound of the first bin is determined such that the first bin is associated with the specified mass error value. In an embodiment, the binning function generates bins associated with the same width. The binning module determines the upper bound of the first bin such that the first bin is associated with the specified width.

Subsequently, the upper bound of the first bin is set as a lower bound of the second bin. The binning module then iterates the process to determine an upper bound of the second bin. Hence, the above process may be iterated such that lower bounds of each of a set of bins are iteratively determined. The above process is iterated until the upper bound of the last bin is reached. Examples of operations for determining lower bounds and/or upper bounds of a set of bins are described above with reference to Operation 206.

One or more embodiments include generating the training set of binned mass spectra based on the training set of mass spectra (Operation 308). Examples of operations for generating a binned mass spectrum based on a mass spectrum are described above with reference to Operation 208. Each mass spectrum, in the training set of mass spectra, is used to generate a binned mass spectrum.

One or more embodiments include associating each binned mass spectrum with a label of the corresponding training classification (Operation 310). Each binned mass spectrum is labeled, or otherwise stored with, a training classification of a biological sample.

In an embodiment, a label and/or other information identifying a training classification associated with a particular mass spectrum is determined. The label and/or other information identifying the training classification is copied and associated with a binned mass spectrum, generated based on the particular mass spectrum.

One or more embodiments include applying a machine learning algorithm to the labeled binned mass spectra to generate a classification algorithm (Operation 312). A machine learning algorithm is applied to the labeled binned mass spectra to generate a classification algorithm. Various types of machine learning algorithms may be used to generate various types of classification algorithms.

As an example, supervised learning and/or unsupervised learning algorithms may be used. As another example, backpropagation may be used to determine an ANN. As another example, regression may be used to determine a regression model. As another example, clustering may be used to determine a classification algorithm. As another example, a learning method may be used to determine a decision tree classifier.

Through the learning process, any attributes of a classification algorithm may be determined. Attributes of a classification algorithm include, for example, types of inputs to the classification algorithm, weights used in the classification algorithm, a number of layers (particularly for an ANN), and connections between neurons (particularly for an ANN), and a sequence of operations.

The classification algorithm generated based on operations of FIG. 3 is configured to determine a microbial classification of a biological sample, as described above with reference to FIG. 2.

In an embodiment, the classification algorithm is stored in association with one or more parameters. As an example, a parameter of the classification algorithm may be a mass error value determined at Operation 304. A parameter of the classification algorithm may be the lower bound for the first bin determined at Operation 306. A parameter of the classification algorithm may be a mass range associated with the training set of mass spectra and/or training set of binned mass spectra. A parameter of the classification algorithm may be a convolution window size used during the learning process. Certain parameters associated with generating the classification algorithm are subsequently used when applying the classification algorithm. As an example, the same parameter used for generating a training set of binned mass spectra may be used for generating a binned mass spectrum, at Operations 204-206, for a biological sample to be classified using the classification algorithm. The parameter may include the binning function, mass error value, lower bound of the first bin, and/or upper bound of the last bin used for generating the training set of binned mass spectra.

In another embodiment, the respective parameters associated with the training set of binned mass spectra are stored in association with the training set of binned mass spectra. The machine learning algorithm is applied to the training set of binned mass spectra, along with the respective parameters associated with the training set of binned mass spectra, to generate the classification algorithm. A mass spectrum of a biological sample to be classified by the classification algorithm does not necessarily need to be associated with the same parameters that were applied to one or more of the training set of mass spectra. Any binning function, mass error value, lower bound of the first bin, and/or upper bound of the last bin may be used for generating the binned mass spectrum for the biological sample to be classified by the classification algorithm. The binned mass spectrum is stored in association with information indicating the binning function, mass error value, lower bound of the first bin, and/or upper bound of the last bin that was used to generate the binned mass spectrum. The classification algorithm is applied to the binned mass spectrum, along with the parameters associated with the binned mass spectrum, to determine a microbial classification for the biological sample.

5. Example Embodiment

A detailed example is described below for purposes of clarity. Components and/or operations described below should be understood as one specific example which may not be applicable to certain embodiments. Accordingly, components and/or operations described below should not be construed as limiting the scope of any of the claims.

Figure 4A:
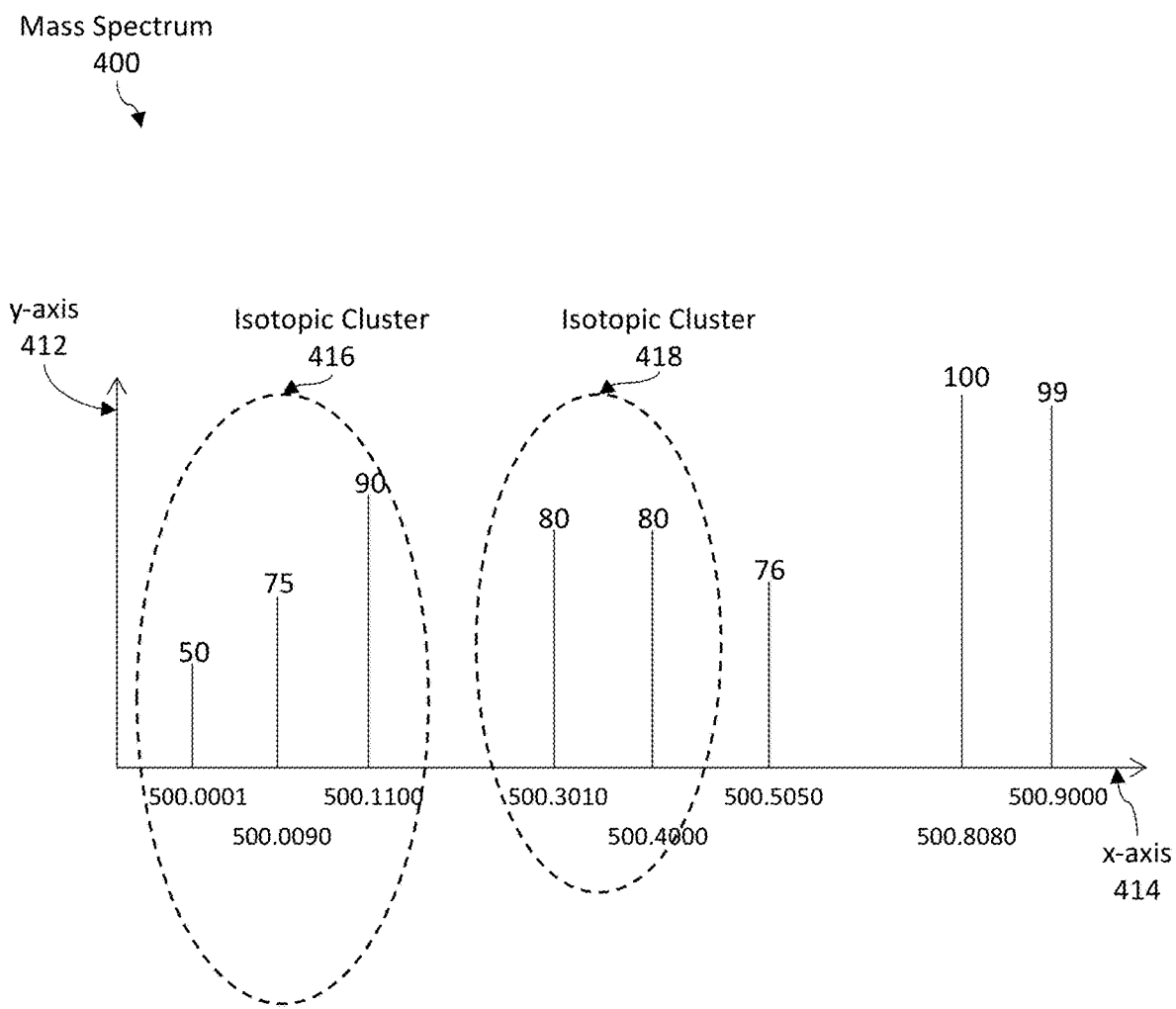
FIG. 4A illustrates an example mass spectrum, in accordance with one or more embodiments.

FIG. 4A illustrates an example mass spectrum, in accordance with one or more embodiments. Mass spectrum 400 includes a y-axis 412 and an x-axis 414. The y-axis 412 indicates an abundance level of ions detected by a mass spectrometer. The x-axis 414 indicates a mass-to-charge ratio of ions detected by the mass spectrometer.

Each vertical bar in mass spectrum 400 corresponds to a mass-to-charge ratio. The length of a vertical bar indicates an abundance level at the corresponding mass-to-charge ratio. As illustrated, mass spectrum 400 indicates the following mass-to-charge ratios and abundance levels:

| Mass-to-charge ratio (Da) | Abundance level |
|---|---|
| 500.0001 | 50 |
| 500.0090 | 75 |
| 500.1100 | 90 |
| 500.3010 | 80 |
| 500.4000 | 80 |
| 500.5050 | 76 |
| 500.8080 | 100 |
| 500.9000 | 99 |

Further as illustrated, mass spectrum 400 indicates two isotopic clusters 416-418. Each isotopic cluster 416-418 indicates mass-to-charge ratios of different isotopes of a same ion. Isotopic cluster 416 includes abundance level 50 at mass-to-charge ratio 500.0001 Da; abundance level 75 at mass-to-charge ratio 500.0090 Da; and abundance level 90 at mass-to-charge ratio 500.1100 Da. Isotopic cluster 418 includes abundance level 80 at mass-to-charge ratio 500.3010 Da; and abundance level 80 at mass-to-charge ratio 500.4000 Da. Deisotoping of mass spectrum 400 would remove the isotopic clusters 416-418. However, the system does not perform deisotoping on mass spectrum 400. Mass spectrum 400, including isotopic clusters 416-418, is analyzed.

Figure 4B:
FIG. 4B illustrates an example binning table, in accordance with one or more embodiments.

FIG. 4B illustrates an example binning table, in accordance with one or more embodiments. A mass error of each bin is determined using:

$$ME = \frac{m_u - m_l}{m_l} \times 10^6.$$

A mass error of each bin is set to equal a fixed value of 200. A lower bound of a first bin is determined as 500.0000 Da. Hence, a set of bins 422-428 are identified, such that each bin is associated with a mass error of 200. As illustrated, bin 422 is associated with a mass-to-charge ratio range of 500.0000-500.1000 Da. Bin 424 is associated with a mass-to-charge ratio range of 500.1000-500.3001 Da. Bin 426 is associated with a mass-to-charge ratio range of 500.3001-500.6004 Da. Bin 428 is associated with a mass-to-charge ratio range of 500.6004-501.0010 Da. Bins 422-428 are associated with different widths. Widths of bins 422-428 are 0.1000 Da, 0.2001 Da, 0.3003 Da, and 0.4006 Da, respectively.

Figure 4C:
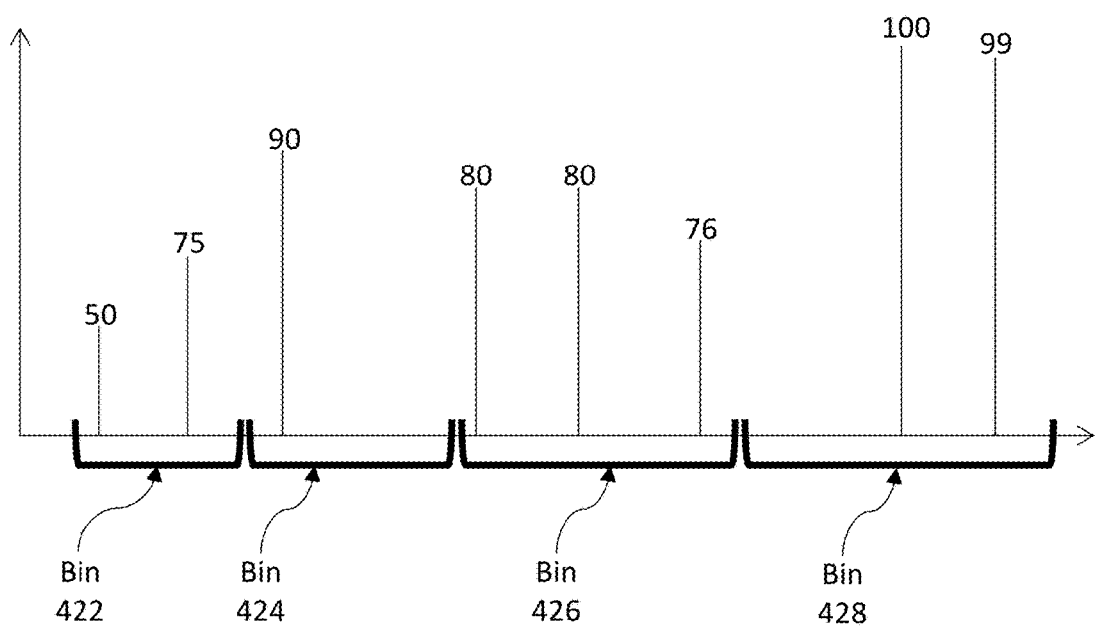
FIG. 4C illustrates an example mass spectrum being partitioned into bins, in accordance with one or more embodiments.

FIG. 4C illustrates an example mass spectrum being partitioned into bins, in accordance with one or more embodiments. Mass spectrum 400 is partitioned using bins 422-428. Mass spectrum 400 indicates an abundance level of 50 at a mass-to-charge ratio of 500.0001 Da. Since the mass-to-charge ratio of 500.0001 Da falls within the range of bin 422 (500.0000-500.1000 Da), the abundance level of 50 at the mass-to-charge ratio of 500.0001 Da is determined to be in bin 422. Similarly, each abundance level indicated by mass spectrum 400 is traversed and partitioned. As illustrated, the abundance levels indicated by mass spectrum 400 are partitioned into bins 422-428, as follows:

| Mass-to-charge ratio (Da) | Abundance level | Bin |
|---|---|---|
| 500.0001 | 50 | Bin 422 |
| 500.0090 | 75 | Bin 422 |
| 500.1100 | 90 | Bin 424 |
| 500.3010 | 80 | Bin 426 |
| 500.4000 | 80 | Bin 426 |
| 500.5050 | 76 | Bin 426 |
| 500.8080 | 100 | Bin 428 |
| 500.9000 | 99 | Bin 428 |

Abundance levels of a particular isotopic cluster may be but are not necessarily categorized into a same bin. As illustrated, two abundance levels of isotopic cluster 416 are put into bin 422. A third abundance level of isotopic cluster 416 is put into bin 424. Meanwhile, all abundance levels of isotopic cluster 418 are put into bin 426.

Each bin may include abundance levels corresponding to zero, one, or more ions. As illustrated, bin 422 includes abundance levels corresponding to isotopic cluster 416 of the same ion. Bin 422 does not include abundance levels corresponding to any other ion. Meanwhile, bin 426 includes abundance levels corresponding to isotopic cluster 418 of one ion. Bin 426 further includes an abundance level of 76 at mass-to-charge ratio of 500.5050 Da corresponding to a different ion. Bin 426 includes abundance levels corresponding to two different ions.

Figure 4D:
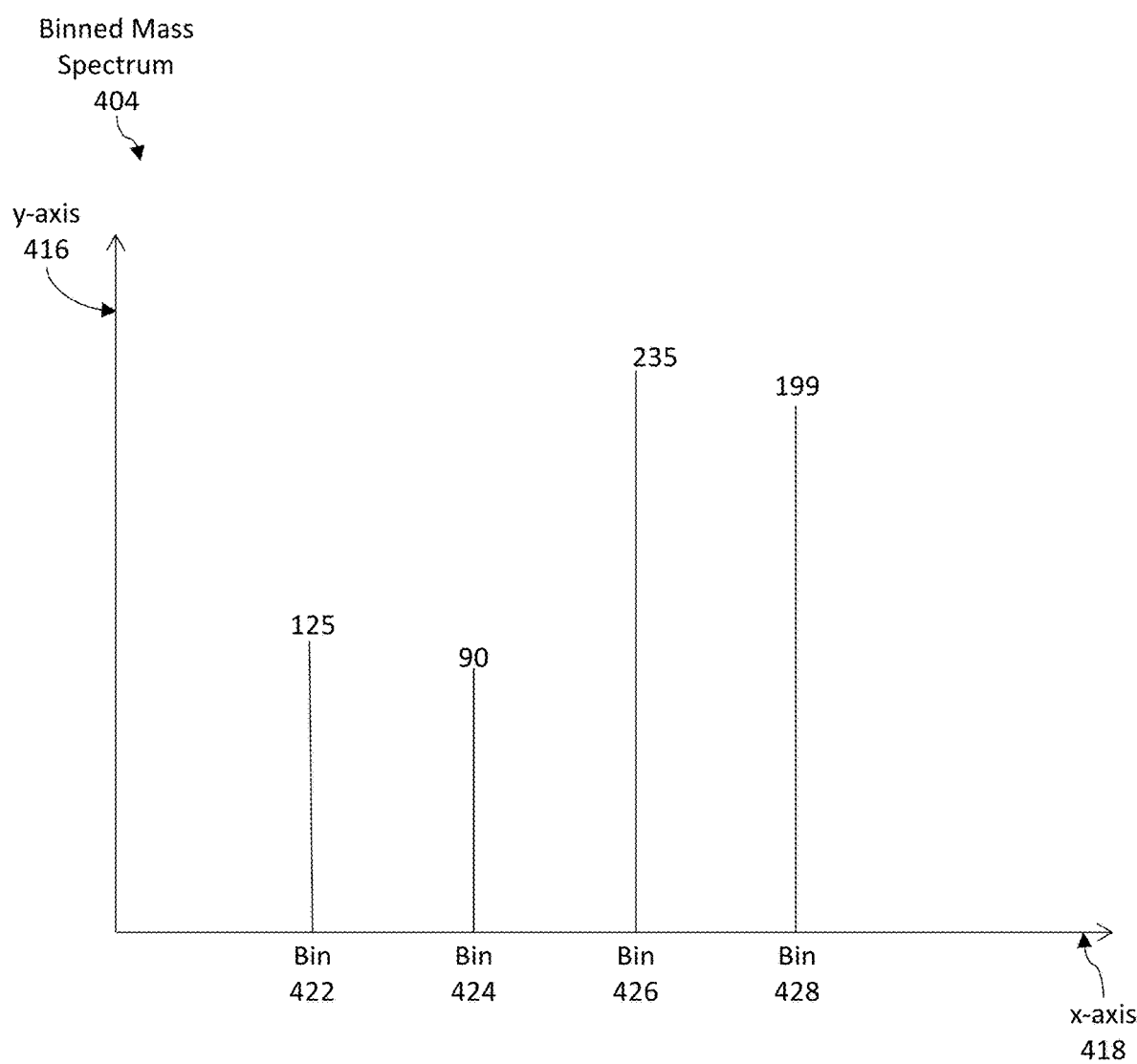
FIG. 4D illustrates an example binned mass spectrum generated based on a mass spectrum, in accordance with one or more embodiments.

FIG. 4D illustrates an example binned mass spectrum generated based on a mass spectrum, in accordance with one or more embodiments. Binned mass spectrum 404 includes a y-axis 416 and an x-axis 418. The y-axis 416 indicates an aggregated abundance level of ions. The x-axis 418 indicates a bin.

Each vertical bar in binned mass spectrum 404 corresponds to one of the bins 422-428. The length of a vertical bar indicates an aggregated abundance level corresponding to a bin.

The abundance levels, indicated by mass spectrum 400, corresponding to a same bin are aggregated. The sum of the abundance levels constitutes an aggregated abundance level for the bin.

As an example, bin 422 includes: the abundance level of 50 at the mass-to-charge ratio of 500.0001 Da, and the abundance level of 75 at the mass-to-charge ratio of 500.0090 Da. The sum of the abundance levels is 125. Hence, an aggregated abundance level of bin 422 is 125. Similarly, each bin is traversed to aggregate the corresponding abundance levels indicated by mass spectrum 400.

As illustrated, the aggregated abundance levels are determined per bin as follows:

| Bin     | Mass-to-charge ratio |
|---------|----------------------|
| Bin 422 | 125                  |
| Bin 424 | 90                   |
| Bin 426 | 235                  |
| Bin 428 | 199                  |

Figure 4E:
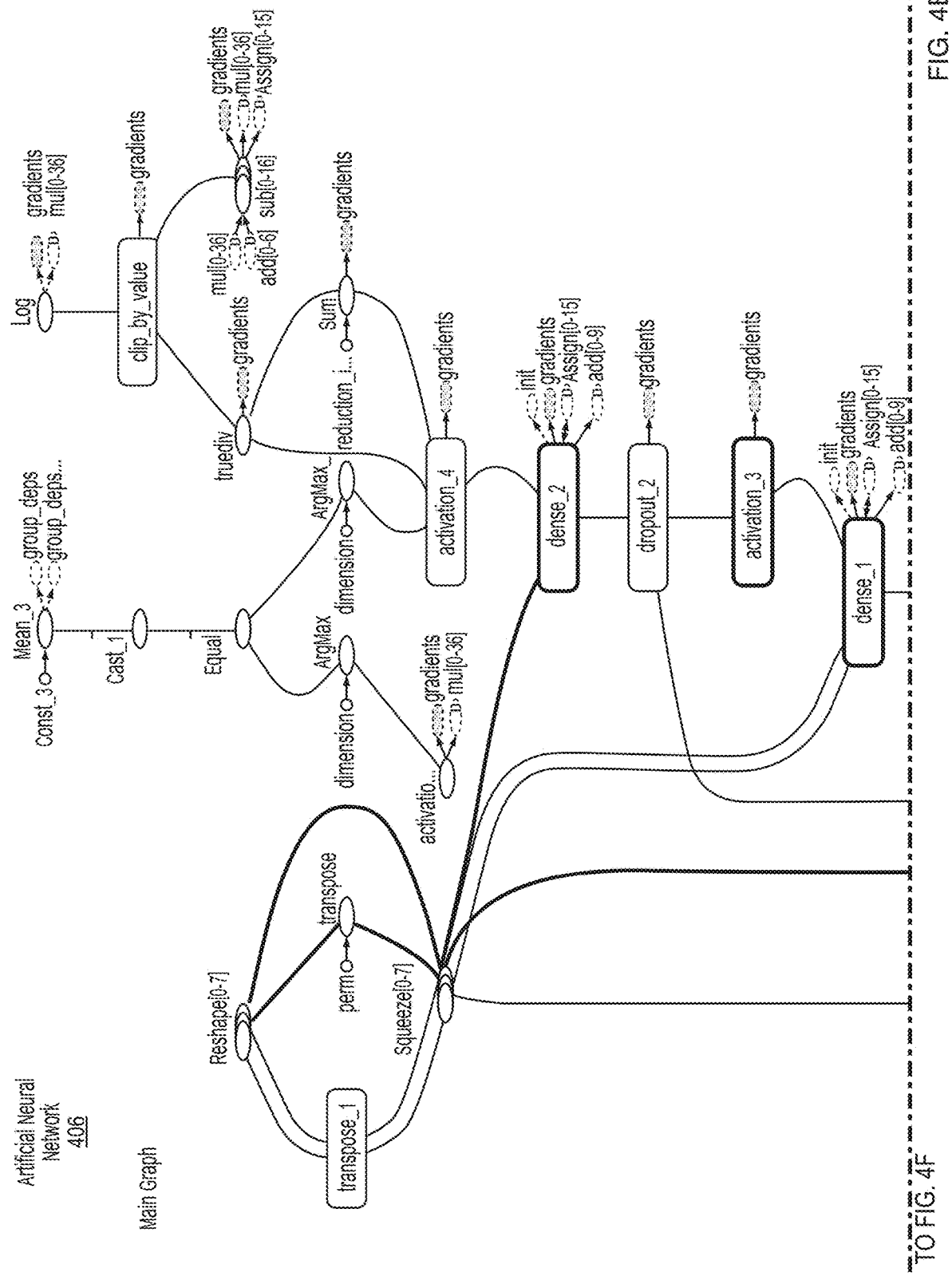
FIGS. 4E-4G illustrate an example artificial neural network (ANN) for determining a microbial classification based on a binned mass spectrum, in accordance with one or more embodiments.
Figure 4F:
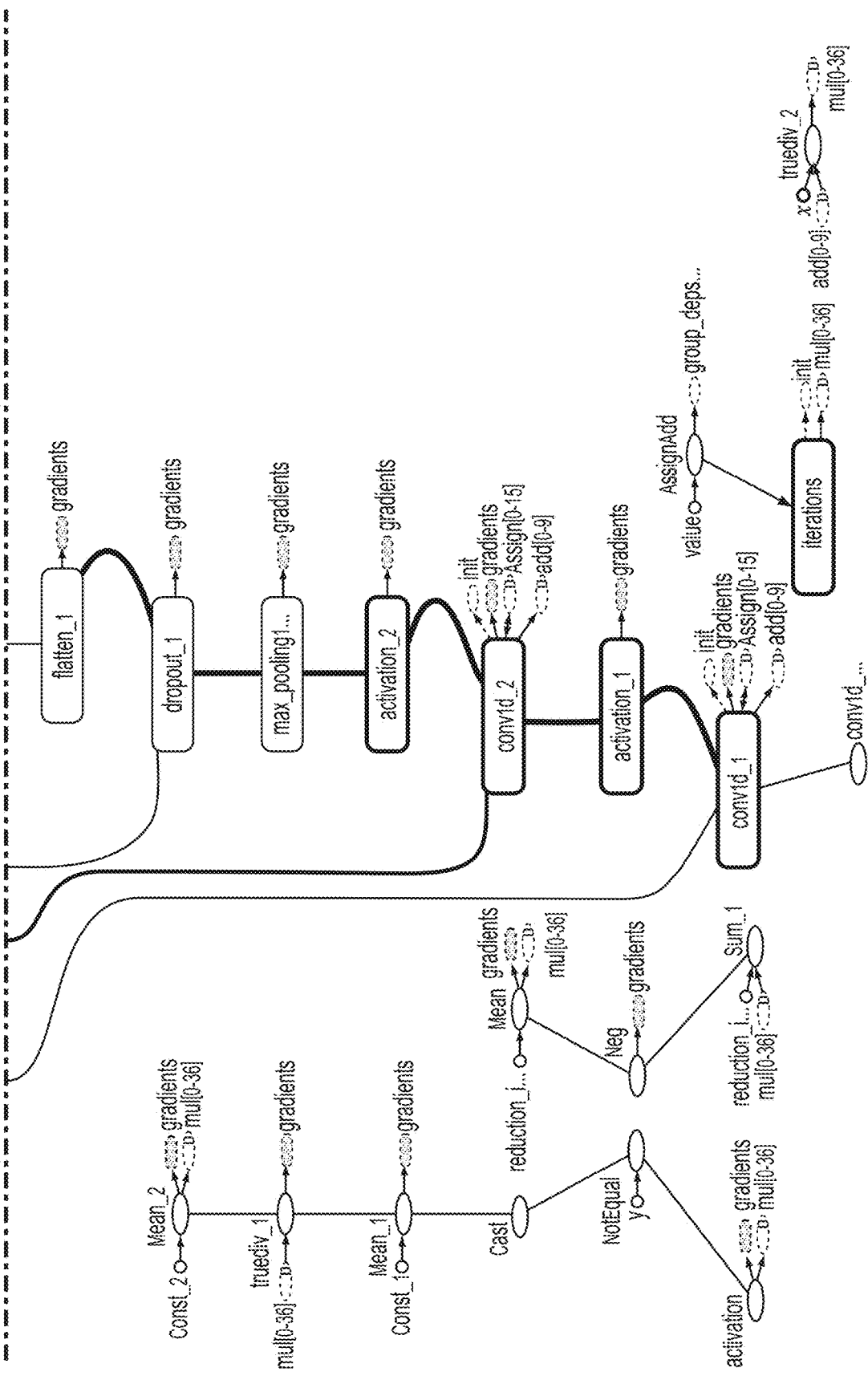
Figure 4G:
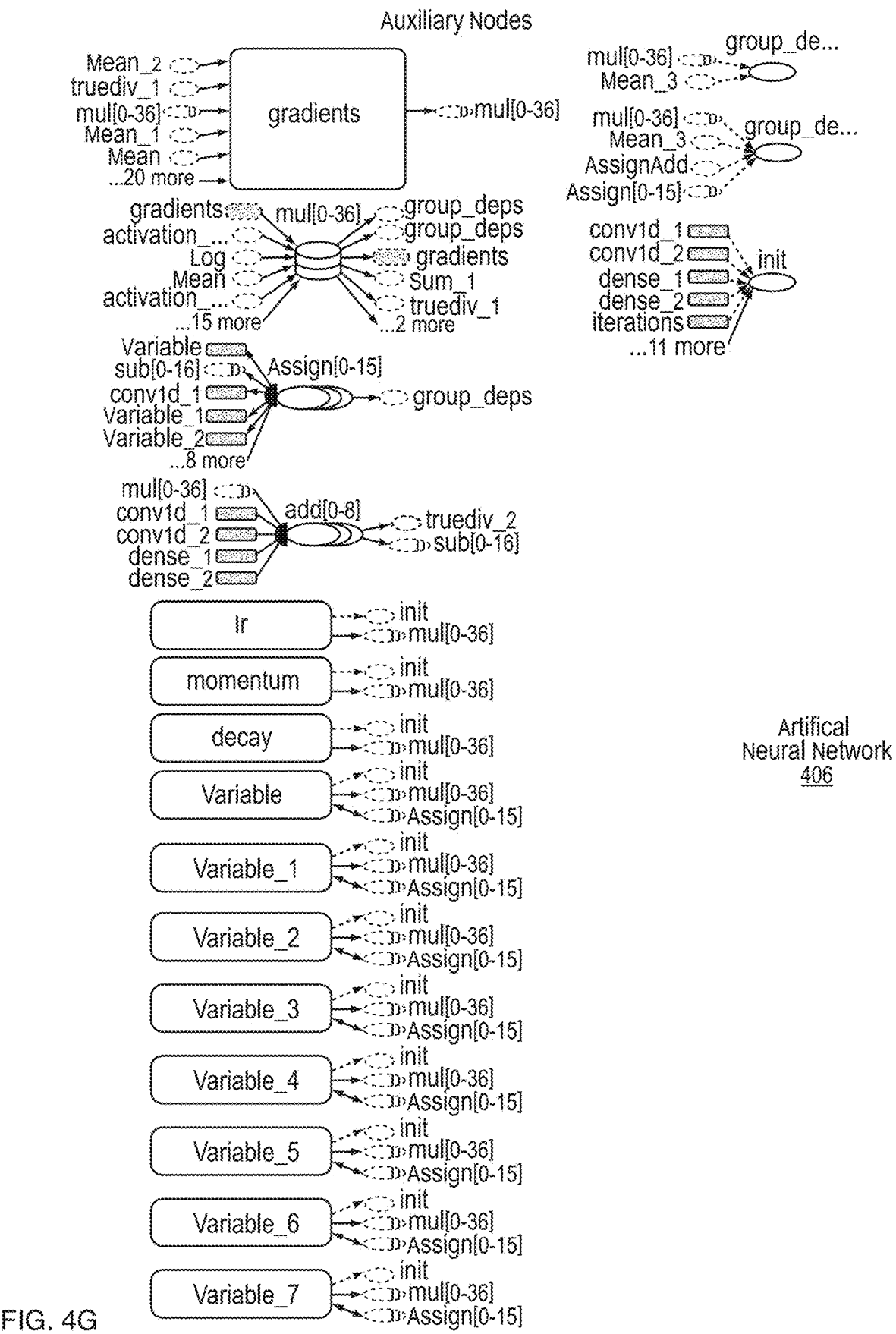

FIGS. 4E-4G illustrate an example artificial neural network (ANN) for determining a microbial classification based on a binned mass spectrum, in accordance with one or more embodiments. As illustrated, an ANN 406 includes multiple layers. The sequential ordering of the layers is as follows: convolution layer 1, activation layer 1, convolution layer 2, activation layer 2, max pooling layer 1, dropout layer 2, flatten layer 1, dense layer 1, activation layer 3, dropout layer 2, dense layer 2, and activation layer 4.

FIG. 4H illustrates an example probability vector generated by an ANN for determining a microbial classification based on a binned mass spectrum, in accordance with one or more embodiments. A probability vector 408 indicates a respective probability for each of a set of candidate microbial classifications for a biological sample. A set of candidate microbial classifications includes, for example, *Haemophilus haemolyticus*, *Staphylococcus capitis*, *Aeromonas simiae*, and *Streptococcus oralis*. As illustrated, there is a $6.27 \times 10^{-4}$ probability that the biological sample includes *Haemophilus haemolyticus*. There is a $9.24 \times 10^{-4}$ probability that the biological sample includes *Staphylococcus capitis*. There is a $5.03 \times 10^{-4}$ probability that the biological sample includes *Aeromonas simiae*. There is a $9.74 \times 10^{-1}$ probability that the biological sample includes *Streptococcus oralis*.

The system verifies whether the probability vector 408 satisfies a criteria. In particular, the highest probability indicated by the probability vector 408 must exceed a threshold value of $9.00 \times 10^{-1}$. The probability vector 408 indicates that the candidate microbial classification associated with the highest probability is *Streptococcus oralis*. The probability associated with *Streptococcus oralis* is $9.74 \times 10^{-1}$ and therefore greater than the threshold value of $9.00 \times 10^{-1}$. Hence, the biological sample is determined as *Streptococcus oralis*.

6. Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs), field programmable gate arrays (FPGAs), or network processing units (NPUs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, FPGAs, or NPUs with custom programming to accomplish the techniques. The special-purpose computing devices may be desktop computer systems, portable computer systems, handheld devices, networking devices or any other device that incorporates hard-wired and/or program logic to implement the techniques.

Figure 5:
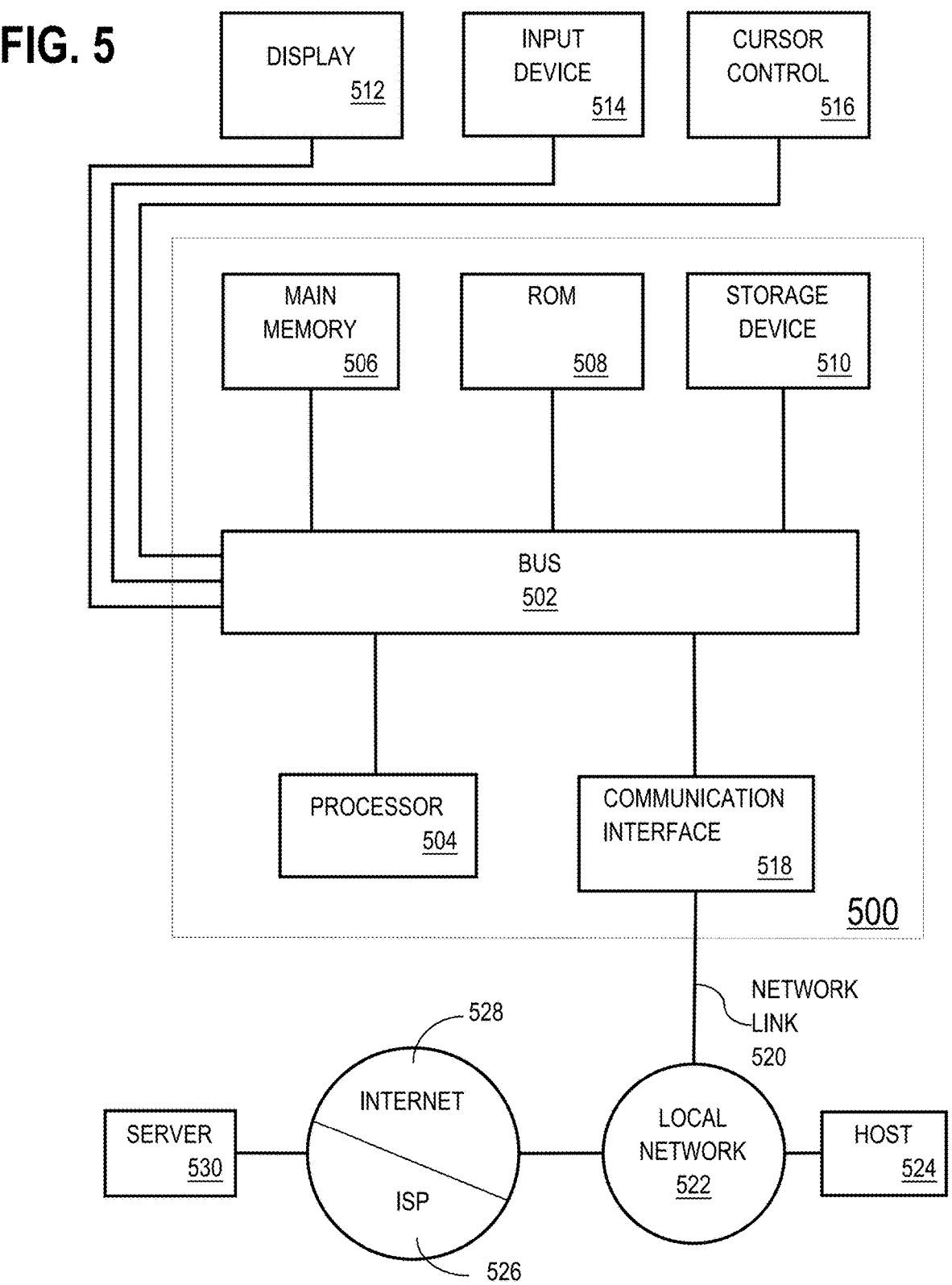
FIG. 5 shows a block diagram that illustrates a computer system in accordance with one or more embodiments.

For example, FIG. 5 is a block diagram that illustrates a computer system 500 upon which an embodiment of the invention may be implemented. Computer system 500 includes a bus 502 or other communication mechanism for communicating information, and a hardware processor 504 coupled with bus 502 for processing information. Hardware processor 504 may be, for example, a general purpose microprocessor.

Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Such instructions, when stored in non-transitory storage media accessible to processor 504, render computer system 500 into a special-purpose machine that is customized to perform the operations specified in the instructions.

Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

Computer system 500 may be coupled via bus 502 to a display 512, such as a cathode ray tube (CRT) or a light emitting diode (LED) monitor, for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

Computer system 500 may implement the techniques described herein using customized hard-wired logic, one or more ASICs or FPGAs, firmware and/or program logic which in combination with the computer system causes or programs computer system 500 to be a special-purpose machine. According to one embodiment, the techniques herein are performed by computer system 500 in response to processor 504 executing one or more sequences of one or more instructions contained in main memory 506. Such instructions may be read into main memory 506 from another storage medium, such as storage device 510. Execution of the sequences of instructions contained in main memory 506 causes processor 504 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical or magnetic disks, such as storage device 510. Volatile media includes dynamic memory, such as main memory 506. Common forms of storage media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, content-addressable memory (CAM), and ternary content-addressable memory (TCAM).

Storage media is distinct from but may be used in conjunction with transmission media. Transmission media participates in transferring information between storage media. For example, transmission media includes coaxial cables, copper wire and fiber optics, including the wires that comprise bus 502. Transmission media can also take the form of acoustic or light waves, such as those generated during radio-wave and infra-red data communications.

Various forms of media may be involved in carrying one or more sequences of one or more instructions to processor 504 for execution. For example, the instructions may initially be carried on a magnetic disk or solid state drive of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a local network 522. For example, communication interface 518 may be an integrated services digital network (ISDN) card, cable modem, satellite modem, or a modem to provide a data communication connection to a corresponding type of telephone line. As another example, communication interface 518 may be a local area network (LAN) card to provide a data communication connection to a compatible LAN. Wireless links may also be implemented. In any such implementation, communication interface 518 sends and receives electrical, electromagnetic or optical signals that carry digital data streams representing various types of information.

Network link 520 typically provides data communication through one or more networks to other data devices. For example, network link 520 may provide a connection through local network 522 to a host computer 524 or to data equipment operated by an Internet Service Provider (ISP) 526. ISP 526 in turn provides data communication services through the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are example forms of transmission media.

Computer system 500 can send messages and receive data, including program code, through the network(s), network link 520 and communication interface 518. In the Internet example, a server 530 might transmit a requested code for an application program through Internet 528, ISP 526, local network 522 and communication interface 518.

The received code may be executed by processor 504 as it is received, and/or stored in storage device 510, or other non-volatile storage for later execution.

7. Miscellaneous; Extensions

Embodiments are directed to a system with one or more devices that include a hardware processor and that are configured to perform any of the operations described herein and/or recited in any of the claims below.

In an embodiment, a non-transitory computer readable storage medium comprises instructions which, when executed by one or more hardware processors, causes performance of any of the operations described herein and/or recited in any of the claims.

Any combination of the features and functionalities described herein may be used in accordance with one or more embodiments. In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. One or more non-transitory machine-readable media storing instructions which, when executed by one or more processors, cause:

obtaining a mass spectrum for a biological sample, wherein the mass spectrum is generated by analyzing the biological sample using a mass spectrometer, and the mass spectrum indicates a plurality of abundance levels respectively corresponding to a plurality of mass-to-charge ratios of ions of the biological sample;

partitioning the plurality of mass-to-charge ratios into a plurality of bins, wherein the plurality of bins are respectively associated with a plurality of mass errors of a same value, and a first mass error, of the plurality of mass errors, is determined based on a first lower bound and a first upper bound of a first bin, of the plurality of bins;

generating a binned mass spectrum based on the mass spectrum, wherein the binned mass spectrum indicates a plurality of computed abundance levels respectively corresponding to the plurality of bins;

applying a classification algorithm to the binned mass spectrum to determine a microbial classification for the biological sample.

2. The one or more media of claim 1, wherein:

the first mass error associated with the first bin is determined based on applying a mass error formula to (a) the first lower bound of the first bin and (b) the first upper bound of the first bin;

a second mass error, of the plurality of mass errors, associated with a second bin, of the plurality of bins, is determined based on applying the mass error formula to (a) a second lower bound of the second bin and (b) a second upper bound of the second bin; and the first mass error and the second mass error are of the same value.

3. The one or more media of claim 1, wherein:

the first mass error associated with the first bin is determined based on dividing (a) a difference between the first lower bound and the first upper bound of the first bin by (b) an average of the first lower bound and the first upper bound of the first bin.

4. The one or more media of claim 1, wherein generating the binned mass spectrum based on the mass spectrum comprises:

identifying a first abundance level, of the plurality of abundance levels, corresponding to a first mass-to-charge ratio, of the plurality of mass-to-charge ratios, indicated by the mass spectrum;

determining that the first mass-to-charge ratio corresponds to the first bin;

identifying a second abundance level, of the plurality of abundance levels, corresponding to a second mass-to-charge ratio, of the plurality of mass-to-charge ratios, indicated by the mass spectrum;

determining that the second mass-to-charge ratio corresponds to the first bin;

aggregating the first abundance level and the second abundance level into a first aggregated abundance level corresponding to the first bin;

determining the first aggregated abundance level as a first computed abundance level, of the plurality of computed abundance levels, for the first bin.

5. The one or more media of claim 1, wherein generating the binned mass spectrum based on the mass spectrum comprises:

determining a sum of a subset of the plurality of abundance levels that correspond to a subset of the plurality of mass-to-charge ratios that are within the first bin;

identifying the sum as a first computed abundance level, of the plurality of computed abundance levels, for the first bin.

6. The one or more media of claim 1, wherein a first width of the first bin and a second width of a second bin, of the plurality of bins, are different.

7. The one or more media of claim 1, wherein the plurality of bins includes the first bin associated with a first lower bound and a second bin associated with a second lower bound that is greater than the first lower bound, and a first width of the first bin is lesser than a second width of the second bin.

8. The one or more media of claim 1, wherein the microbial classification comprises at least one of a genus and a species.

9. The one or more media of claim 1, wherein applying the classification algorithm to the binned mass spectrum to determine the microbial classification for the biological sample comprises:

determining a probability vector associated with a plurality of candidate microbial classifications based on applying the classification algorithm to the binned mass spectrum;

identifying one of the plurality of candidate microbial classifications associated with a highest probability as the microbial classification for the biological sample.

10. The one or more media of claim 1, wherein applying the classification algorithm to the binned mass spectrum to determine the microbial classification for the biological sample comprises:

applying the classification algorithm to the binned mass spectrum to determine a probability vector associated with a plurality of candidate microbial classifications;

identifying a candidate microbial classification, of the plurality of candidate microbial classifications, associated with a highest probability;

responsive to determining that the highest probability exceeds a threshold value, determining the candidate microbial classification as the microbial classification for the biological sample.

11. The one or more media of claim 1, further storing instructions which, when executed by one or more processors, cause:

obtaining a second mass spectrum associated with the biological sample, wherein the second mass spectrum is generated by analyzing the biological sample using a second mass spectrometer;

generating a second binned mass spectrum based on the second mass spectrum;

applying the classification algorithm to the second binned mass spectrum to determine a probability vector associated with a plurality of candidate microbial classifications;

identifying a candidate microbial classification, of the plurality of candidate microbial classifications, associated with a highest probability;

responsive to determining that the highest probability is below a threshold value:
    refraining from determining the candidate microbial classification as the microbial classification for the biological sample; and
    obtaining the mass spectrum for analysis.

12. The one or more media of claim 1, further storing instructions which, when executed by one or more processors, cause:

obtaining a plurality of mass spectra associated with the biological sample, wherein the plurality of mass spectra are generated by analyzing the biological sample using the mass spectrometer, and the plurality of mass spectra includes the mass spectrum;

selecting the mass spectrum, from the plurality of mass spectra, for analysis, the selecting operation comprising:

obtaining a chromatogram, wherein the chromatogram is generated by performing a plurality of scans, over a plurality of time intervals, on the biological sample using the mass spectrometer, and the chromatogram indicates a second plurality of abundance levels respectively corresponding to the plurality of time intervals;

determining a particular time interval, of the plurality of time intervals, associated with a highest abundance level, of the second plurality of abundance levels;

determining a particular scan, of the plurality of scans, associated with the particular time interval;

determining that the mass spectrum is obtained using the particular scan.

13. The one or more media of claim 1, wherein the classification algorithm comprises an artificial neural network (ANN).

14. The one or more media of claim 1, wherein the microbial classification is determined without applying the classification algorithm to any mass spectrum corresponding to fragmented ions of the biological sample.

15. The one or more media of claim 1, wherein the mass spectrum corresponds to unfragmented ions of the biological sample.

16. The one or more media of claim 1, wherein the microbial classification is determined without performing any charge-state deconvolution or de-isotoping on the mass spectrum.

17. The one or more media of claim 1, wherein the mass spectrum does not include any abundance levels for mass-to-charge ratios above 1,500 m/z.

18. The one or more media of claim 1, further storing instructions which, when executed by one or more processors, cause:
determining a treatment based on the microbial classification for the biological sample.

19. The one or more media of claim 1, further storing instructions which, when executed by one or more processors, cause:
obtaining a first training set of mass spectra associated with a first training biological sample of the microbial classification, wherein the first training set of mass spectra are generated by analyzing the first training biological sample using a second mass spectrometer;
obtaining a second training set of mass spectra associated with a second training biological sample of a second microbial classification, wherein the second training set of mass spectra are generated by analyzing the second training biological sample using a third mass spectrometer;
generating a first training set of binned mass spectra based on the first training set of mass spectra, wherein bins of the first training set of binned mass spectra are respectively associated with a second plurality of mass errors of the same value;
generating a second training set of binned mass spectra based on the second training set of mass spectra, wherein bins of the second training set of binned mass spectra are respectively associated with a third plurality of mass errors of the same value;
associating the first training set of binned mass spectra with a first label of the first microbial classification;
associating the second training set of binned mass spectra with a second label of the second microbial classification;
generating the classification algorithm for classifying a target biological sample, based at least on (a) the first training set of binned mass spectra and the associated first label of the first microbial classification and (b) the second training set of binned mass spectra and the associated second label of the second microbial classification.

20. A method, comprising:
obtaining a mass spectrum associated with a biological sample, wherein the mass spectrum is generated by analyzing the biological sample using a mass spectrometer, and the mass spectrum indicates a plurality of abundance levels respectively corresponding to a plurality of mass-to-charge ratios of ions of the biological sample;
partitioning the plurality of mass-to-charge ratios into a plurality of bins, wherein the plurality of bins are respectively associated with a plurality of mass errors of a same value, and a first mass error, of the plurality of mass errors, is determined based on a first lower bound and a first upper bound of a first bin, of the plurality of bins;
generating a binned mass spectrum based on the mass spectrum, wherein the binned mass spectrum indicates a plurality of computed abundance levels respectively corresponding to the plurality of bins;
applying a classification algorithm to the binned mass spectrum to determine a microbial classification for the biological sample;
wherein the method is performed by at least one device including a hardware processor.

21. A system, comprising:
at least one device including a hardware processor; and
the system being configured to perform operations comprising:
obtaining a mass spectrum associated with a biological sample, wherein the mass spectrum is generated by analyzing the biological sample using a mass spectrometer, and the mass spectrum indicates a plurality of abundance levels respectively corresponding to a plurality of mass-to-charge ratios of ions of the biological sample;
partitioning the plurality of mass-to-charge ratios into a plurality of bins, wherein the plurality of bins are respectively associated with a plurality of mass errors of a same value, and a first mass error, of the plurality of mass errors, is determined based on a first lower bound and a first upper bound of a first bin, of the plurality of bins;
generating a binned mass spectrum based on the mass spectrum, wherein the binned mass spectrum indicates a plurality of computed abundance levels respectively corresponding to the plurality of bins;
applying a classification algorithm to the binned mass spectrum to determine a microbial classification for the biological sample.

22. One or more non-transitory machine-readable media storing instructions which, when executed by one or more processors, cause:
obtaining a mass spectrum for a biological sample, wherein the mass spectrum is generated by analyzing the biological sample using a mass spectrometer, and the mass spectrum indicates a plurality of abundance levels respectively corresponding to a plurality of mass-to-charge ratios of ions of the biological sample;
applying a binning function to the mass spectrum to generate a binned mass spectrum, wherein the binned mass spectrum indicates a plurality of computed abundance levels respectively corresponding to a plurality of bins;

applying a classification algorithm to the binned mass spectrum to determine a microbial classification for the biological sample.

\* \* \* \* \*